United States Patent [19]
Chow et al.

[11] Patent Number: 5,895,415
[45] Date of Patent: *Apr. 20, 1999

[54] MULTI-PHASIC MICROPHOTODIODE RETINAL IMPLANT AND ADAPTIVE IMAGING RETINAL STIMULATION SYSTEM

[75] Inventors: Vincent Chow, Hanover Park; Alan Y. Chow, Wheaton, both of Ill.

[73] Assignee: Optobionics Corporation, Wheaton, Ill.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/465,766

[22] Filed: Jun. 6, 1995

[51] Int. Cl.$^6$ .................................... A61N 1/18
[52] U.S. Cl. .......................... 607/54; 607/116; 607/148
[58] Field of Search ........................ 607/54, 116, 148, 607/53; 623/4

[56] References Cited

U.S. PATENT DOCUMENTS

| | | |
|---|---|---|
| 2,760,483 | 10/1956 | Tassicker . |
| 3,594,823 | 7/1971 | Collins . |
| 3,628,193 | 12/1971 | Collins . |
| 3,766,311 | 10/1973 | Boll . |
| 3,848,608 | 11/1974 | Leonard . |
| 3,914,800 | 10/1975 | Collins . |

(List continued on next page.)

FOREIGN PATENT DOCUMENTS

| | | |
|---|---|---|
| 0 233 789 | 8/1987 | European Pat. Off. . |
| 0 501 904 A2 | 9/1992 | European Pat. Off. . |

OTHER PUBLICATIONS

Granit R. Helme T. "Changes In Retinal Excitability Due To Polarization And Some Observations On The Relation Between The Processes in Retina And Nerve", *J. Neurophysiol*, 1939;; 2:556–565.

Knighton R.W. "An Electrically Evoked Slow Potential Of The Frog's Retina. I. Properties Of Response", *J. Neurophysiol*, 1975; 38–185–197.

Brindley, G.S. "The Site Of Electrical Excitation Of The Human Eye", *J. Physiol*, 1955; 127–189–200.

Brindley G.S., "Beats Produced By Simultaneous Stimulation Of The Human Eye With Intermittent Light And Intermittent Or Alternating Electric Current", *J. Physiol*, 1962; 164: 156–167.

(List continued on next page.)

*Primary Examiner*—Marvin M. Lateef
*Assistant Examiner*—Kennedy J. Schaetzle
*Attorney, Agent, or Firm*—Brinks Hofer Gilson & Lione

[57] ABSTRACT

An artificial retina device and a method for stimulating and modulating its function is disclosed. The artificial retina device is comprised of plural multi-phasic microphotodiode subunits. In persons suffering from blindness due to outer retinal layer damage, a plurality of such devices, when surgically implanted into the subretinal space, may allow useful formed artificial vision to develop. One device, called a MMRI-4, transduces light into electric currents to stimulate the retina. The four microphotodiode subunits of the MMRI-4 are oriented so that each flattened sides of the MMRI-4 has two subunits in a PiN configuration and two subunits in a NiP configuration. By projecting real or computer controlled visible light images, and computer controlled infrared light images or illumination, simultaneously or in rapid alternation onto the MMRI-4s, the nature of induced retinal images may be modulated and improved. An Adaptive Imaging Retinal Stimulation System (AIRES), with a Projection and Tracking Optical System (PTOS), which may be worn as a headset is used for this purpose, and is also disclosed. Color images may even be induced by programming the stimulating pulse durations and frequencies of the AIRES system.

46 Claims, 18 Drawing Sheets

U.S. PATENT DOCUMENTS

| | | |
|---|---|---|
| 4,001,867 | 1/1977 | Kravitz et al. |
| 4,251,887 | 2/1981 | Anis |
| 4,272,910 | 6/1981 | Danz |
| 4,551,149 | 11/1985 | Sciarra |
| 4,600,004 | 7/1986 | Lopez et al. |
| 4,601,545 | 7/1986 | Kern |
| 4,628,933 | 12/1986 | Michelson |
| 4,750,498 | 6/1988 | Graham |
| 4,836,202 | 6/1989 | Krasner |
| 4,873,448 | 10/1989 | Shirai |
| 5,016,633 | 5/1991 | Chow |
| 5,024,223 | 6/1991 | Chow |
| 5,109,844 | 5/1992 | De Juan et al. |
| 5,159,927 | 11/1992 | Schmid ................................ 607/53 |
| 5,223,728 | 6/1993 | Gempe |
| 5,256,882 | 10/1993 | Miyasaka |
| 5,338,991 | 8/1994 | Lu |
| 5,351,309 | 9/1994 | Lee et al. |
| 5,397,350 | 3/1995 | Chow et al. |
| 5,411,540 | 5/1995 | Edell et al. |
| 5,476,494 | 12/1995 | Edell et al. |
| 5,491,349 | 2/1996 | Komoto et al. |
| 5,556,423 | 9/1996 | Chow et al. |
| 5,717,201 | 2/1998 | Lin et al. |

OTHER PUBLICATIONS

Potts, A.M., Inoue J., Buffum D., "The Electrically Evoked Response Of The Visual System (EER)", *Invest Ophthalmol Vis Sci.*, 1968; 7:269–278.

Humayun M.S., Propst R.H., Hickingbotham, D., deJuan E. Jr., Dagnelie G., "Visual Sensations Produced By Electrical Stimulation Of The Retinal Surface In Patients With End-Stage Retinitis Pigmentosa (RP)", ARVO Abstracts, *Invest Ophthalmol Vis. Sci.*, 1993; 34 (Suppl):835.

Tasman E., ed. *Duane's Foundations of Clinical Ophthalmology*, vol. 3, Philadelphia, Lippincott, 1992; chapter 13:20–25, chapter 60:1–12.

Stone J.L., Barlow, W.E., Humayun, M.S., deJuan E., Jr., Milam, A.H., "Morphometric Analysis Of Macular Photoreceptor And Ganglion Cells In Retinas With Retinitis Pigmentosa", *Arch Ophthalmol*, 1992; 110:1634–1639.

Pagon, R.A., "Retinitis Pigmentosa", *Surv Ophthalmol,*. 1988; 33:137–177.

Eagle, R.C., Lucier, A.C., Bernardino, V.B., et al., "Retinal Pigment Epithelial Abnormalities In Fundus Flavimaculatus", *Ophthalmol*, 1980; 87:1189–1200.

Hagins, W.A., Penn, R.D., Yoshikami, S. "Dark Current And Photocurrent In Retinal Rods", *Biophys J.*, 1970;10:380–412.

Tomita, T., "Electrical Activity Of Vertebrate Photoreceptor", *Q Rev Biophys.*, 1970;3:179–222.

Baylor, D.A., Fuortes, M.G.F., "Electrical Responses Of Single Cones In The Retina Of The Turtle", *J Physiol*, 1970; 207:77–92.

Chow, A.Y., "Electrical Stimulation Of The Rabbit Retina With Subretinal Electrodes And High Density Microphotodiode Array Implants", ARVO Abstracts, *Invest Ophthalmol Vis Sci.* 199334 (Suppl):835.

Rubin, M.L., *Optics for Clinicians*, Gainsville, TRIAD Scientific Publishers, 1974;119–123.

Boettner, E.A, Wolter, J.R. "Transmission Of The Ocular Media", *Invest Ophthalmol*, 1962; 1:776–783.

Shannon, R.V. "A Model Of Safe Levels For Electrical Stimulation", *IEEE Tarns Biomed Eng.*, 1992; 39:424–426.

Armington, J.C., Brigell, M. "Effects Of Stimulus Location And Pattern Upon The Visually Evoked Cortical Potential And The Electroretinogram", *Int J. Neurosci*, 1981; 14:169–178.

Fenwick, P.B.C., Stone, S.A. Bushman, J., Enderby, D., "Changes In The Patter Reversal Visual Evoked Potential As A Function Of Inspired Nitrous Oxide Concentration", *Electroencephalogr Clin Neurophysiol*, 1984; 57178–183.

Rovamo, J., Virsu, A., "An Estimation And Application Of The Human Cortical Magnification Factor", *Exp Brain Res.*, 1979;37:495–510.

Dowling, J.E., Ripps, H. "Visual Adaptation In The Retina Of The Skate", *J Gen Physiol*, 1970;56:491–520.

Humayun, M., Propst R., De Juan, E., et al. "Bipolar Surface Electrical Stimulation Of The Vertebrate Retina", *Arch Ophthalmol*, 1994; 112:110–116.

Narayanan, M.V., Rizzo, J.F., Edell, D., et al. "Development Of A Silicon Retinal Implant: Cortical Evoked Potentials Following Focal Stimulation Of The Rabbit Retina With Light And Electricity", ARVO Abstracts, *Invest Ophthalmol Vis Sci.*, 1994;35(Suppl):1380.

Dawson, W.W., Radtke, N.D., "The Electrical Stimulation Of The Retina by Indwelling Electrodes", *Invest Ophthalmol Vis Sci.*, 1977;16:249–252.

Brady, G.S., Clauser, H.R., *Materials Handbook, Thirteenth Edition*, New York, McGraw–Hill, 1991; 739–740.

Paton, D., Goldberg, M.F., *Management Of Ocular Injuries*, Philadelphia, W.B. Saunders Co., 1976; 134–135.

Terr, L.I., Linthicum, F.H., House, W.F., "Histopathologic Study Of The Cochlear Nuclei After 10 Years Of Electrical Stimulation Of The Human Cochlea", *Am J Otol.*, 1988.; 9:1–7.

Agnew, W.F. McCreery, D.B. *Neural Prostheses Fundamental Studies*, Englewood Cliffs, Prentice Hall, 1990; 25–65.

Curcio, C.A., Sloan, K.R., Kaliha, R.E. Hendrickson, A.E., "Human Photoreceptor Topography", *J of Comparative Neurology*, 1990;292:497–523.

Brown, et al., "Monolithically Integrated 1×12 Array Of Planar InGaAs/InP Photodiodes", *Journal of Lightwave Technology*, vol. LT–4, No. 3, Mar. 1986, pp. 283–286.

Melen, et al. "A Transparent Electrode CCD Image Sensor For A Reading Aid For The Blind", *IEEE Journal Of Solid–State Circuits*, vol. SC–9, No. 2, Apr. 1974, pp. 41–48.

Kataoka, "An Attempt Towards An Artificial Retina: 3–D IC Technology For An Intelligent Image Sensor", *Transducers '85: International Conference On Solid–State Sensors And Actuators 1985*, pp. 440–442.

Article published in *Science News*, Feb. 2, 1974, vol. 105, No. 5, p. 105.

Article published in Science, Jul., 1981.

ADAPTIVE IMAGING RETINAL STIMULATON SYSTEM (AIRES)

MULTI-PHASIC MICROPHOTODIODE RETINAL IMPLANT AND ADAPTIVE IMAGING RETINAL STIMULATION SYSTEM

BACKGROUND OF THE INVENTION

The present invention is a medical product that can be used to correct vision loss or even complete blindness caused by certain retinal diseases. A variety of retinal diseases cause vision loss or blindness by destruction of the vascular layers of the eye including the choroid, choriocapillaris, and the outer retinal layers including Bruch's membrane and retinal pigment epithelium. Loss of these layers is followed by degeneration of the outer portion of the inner retina beginning with the photoreceptor layer. Variable sparing of the remaining inner retina composed of the outer nuclear, outer plexiform, inner nuclear, inner plexiform, ganglion cell and nerve fiber layers, may occur. The sparing of the inner retina allows electrical stimulation of this structure to produce sensations of light.

Prior efforts to produce vision by electrically stimulating various portions of the retina have been reported. One such attempt involved an externally powered photosensitive device with its photoactive surface and electrode surfaces on opposite sides. The device theoretically would stimulate the nerve fiber layer via direct placement upon this layer from the vitreous body side. The success of this device is unlikely due to it having to duplicate the complex frequency modulated neural signals of the nerve fiber layer. Furthermore, the nerve fiber layer runs in a general radial course with many layers of overlapping fibers from different portions of the retina. Selection of appropriate nerve fibers to stimulate to produce formed vision would be extremely difficult, if not impossible.

Another device involved a unit consisting of a supporting base onto which a photosensitive material such as selenium was coated. This device was designed to be inserted through an external scleral incision made at the posterior pole and would rest between the sclera and choroid, or between the choroid and retina. Light would cause a potential to develop on the photosensitive surface producing ions that would then theoretically migrate into the retina causing stimulation. However, because that device had no discrete surface structure to restrict the directional flow of charges, lateral migration and diffusion of charges would occur thereby preventing any acceptable resolution capability. Placement of that device between the sclera and choroid would also result in blockage of discrete ion migration to the photoreceptor and inner retinal layers. That was due to the presence of the choroid, choriocapillaris, Bruch's membrane and the retinal pigment epithelial layer all of which would block passage of those ions. Placement of the device between the choroid and the retina would still interpose Bruch's membrane and the retinal pigment epithelial layer in the pathway of discrete ion migration. As that device would be inserted into or through the highly vascular choroid of the posterior pole, subchoroidal, intraretinal and intraorbital hemorrhage would likely result along with disruption of blood flow to the posterior pole. One such device was reportedly constructed and implanted into a patient's eye resulting in light perception but not formed imagery.

A photovoltaic device artificial retina was also disclosed in U.S. Pat. No. 5,024,223. That device was inserted into the potential space within the retina itself. That space, called the subretinal space, is located between the outer and inner layers of the retina. The device was comprised of a plurality of so-called Surface Electrode Microphotodiodes ("SEMCPs") deposited on a single silicon crystal substrate. SEMCPs transduced light into small electric currents that stimulated overlying and surrounding inner retinal cells. Due to the solid substrate nature of the SEMCPs, blockage of nutrients from the choroid to the inner retina occurred. Even with fenestrations of various geometries, permeation of oxygen and biological substances was not optimal.

Another method for a photovoltaic artificial retina device was reported in U.S. Pat. No. 5,397,350, which is incorporated herein by reference. That device was comprised of a plurality of so-called Independent Surface Electrode Microphotodiodes (ISEMCPs), disposed within a liquid vehicle, also for placement into the subretinal space of the eye. Because of the open spaces between adjacent ISEMCPs, nutrients and oxygen flowed from the outer retina into the inner retinal layers nourishing those layers. In another embodiment of that device, each ISEMCP included an electrical capacitor layer and was called an ISEMCP-C. ISEMCP-Cs produced a limited opposite direction electrical current in darkness compared to in the light, to induce visual sensations more effectively, and to prevent electrolysis damage to the retina due to prolonged monophasic electrical current stimulation.

These previous devices (SEMCPs, ISEMCPs, and ISEMCP-Cs) depended upon light in the visual environment to power them. The ability of these devices to function in continuous low light environments was, therefore, limited. Alignment of ISEMCPs and ISEMCP-Cs in the subretinal space so that they would all face incident light was also difficult.

SUMMARY OF THE INVENTION

This invention is, among other things, a system that allows for implantation of microscopic implants into the diseased eye so that the system can function in continuous low light levels, and also produce improved perception of light and dark details. This invention has two basic components: (1) multi-phasic microphotodiode retinal implants ("MMRIs") of microscopic sizes that are implanted into the eye, and (2) an externally worn adaptive imaging retinal stimulation system ("AIRES") that, among other things, uses infrared light to stimulate the MMRIs to produce "dark current" in the retina during low light conditions, and to improve perception of light and dark details.

In its basic form, a MMRI of this invention has, depending upon its orientation, a PiN configuration where the P-side of the implant has a light filter layer that permits visible light to pass, and where the N-side of the implant has a light filter that permits only infrared ("IR") light to pass, and preferably only selected wavelength(s) of IR light. In practice, a population of such MMRIs are implanted in the so-called "subretinal space" between the outer and inner retina in the eye such that, randomly, about half of them (i.e. the first subpopulation) will be oriented so that their P sides face light incident to the eye, and about the other half (i.e. the second subpopulation) will be oriented so that their N-sides face light incident to the eye.

In this location and orientation, the first subpopulation of MMRIs convert energy from incoming visible light into small electrical currents to stimulate the sensation of light in the eye to produce formed vision. In other words, the first subpopulation converts visible light to electrical current to stimulate the retina with "light currents" to induce the perception of visible light. The second subpopulation of MMRIs converts infrared light provided by AIRES into electrical currents to stimulate the retina with "dark currents" during low light conditions to induce the perception of darkness.

The adaptive imaging retinal stimulation system or AIRES is comprised of a projection and tracking optical system ("PTOS"), a neuro-net computer ("NNC"), an imaging CCD camera ("IMCCD"), and an input stylus pad ("ISP").

In one embodiment of this invention, each microscopic implant comprises plural paired MMRI subunits disposed together in a single flattened cubic unit. The microscopic implants are fabricated so that each MMRI member of each pair has its positive pole electrode on one of the flattened surfaces, and its negative pole electrode on the other flattened surface. Each MMRI member of each pair is disposed so that it is oriented in the opposite direction from the other MMRI member of the pair, the negative (N) electrode of the first MMRI pair member being on or close to the same surface as the positive (P) electrode of the second MMRI pair member, and the positive electrode of the first MMRI pair member being on or close to the same surface as the negative electrode of the second MMRI pair member. Each of the flattened sides of a single microscopic implant therefore, has at least one associated positive microphotodiode electrode from one MMRI and one negative microphotodiode electrode from another MMRI. This symmetry ensures that each such microscopic implant functions in exactly the same manner regardless of which of the flattened surfaces faces incident light. Multiple layer dielectric filters are disposed on the P surfaces and N surfaces of the MMRI subunits to allow visible light (400 to 740 nm) to pass through to the P surfaces and infrared light (740–900 nm) to pass through to the N surfaces. In this manner, the PiN configuration of each MMRI subunit responds to visible light while the NiP configuration responds to infrared light. In the preferred embodiment, the flattened microscopic implant structures typically have a thickness to width and depth ratio of 1:3 and have a preference to orient themselves, within the subretinal space, with one of their flattened photoactive surfaces positioned to accept incident light. The P and N electrodes of each MMRI subunit are on or close to the microscopic implant's light sensitive surfaces. Electric currents produced by the PiN configuration will stimulate the sensation of "light" in the overlying and/or adjacent retinal cells, while electric currents produced by the NiP configuration will stimulate the sensation of "darkness" in the vicinity of those same cells.

The power for the "light currents" is derived from the visible spectrum of light from incoming images. The power for the "dark currents" is provided by superimposed infrared (IR) light and/or images projected into the eye by an external computer-controlled optical headset system. This external computer-controlled headset projection system is the second component of the artificial retinal device of this invention and is called the Adaptive Imaging Retinal Stimulation System "AIRES".

AIRES is comprised of component sub-systems of: a Projection and Tracking Optical System (PTOS), a Neuro-Net Computer (NNC), an Imaging CCD Camera (IMCCD), and an Input Stylus Pad (ISP). During operation, AIRES "sees" and interprets details and characteristics of images via its own IMCCD and processes this information with its NNC. It then projects modulated infrared light and/or images, and visible light images if necessary into the eye to modify implant function. By the use of a partially reflective and transmissive mirror in the PTOS, AIRES projects IR and visible light/images that are superimposed over the visible spectrum images passing into the eye from the environment. Initially, AIRES will be programmed using "patient input" from an input device, such as a stylus pad, to "train" the NNC on how to modify implant function to produce accurate images. After training, AIRES will have an improved capability to modulate implant function with little additional patient assistance. The primary advantages of this MMRI plus AIRES combination system over the previous art is that the combined system can still function in low light environments and that "light" and "dark" currents may be finely tuned by AIRES to provide optimal images. The production of opposing light and dark currents will also decrease any damaging effects from electrolysis, and improve implant biocompatibility.

In the preferred embodiment, the AIRES PTOS headset is worn by the patient, and projects variable intensity IR and visible-light images and illumination into the eye, by using an IR and visible-light capable CRT (IRVCRT). These IR and visible-light images and illumination will modify the function of the MMRI subunits of the implant by modulating their current output. In darkness, IR illumination is the predominate power source and powers the MMRI NiP configuration to produce electric currents that will stimulating the visual sensation of darkness. However, the IR induced NiP current is modified by the PTOS through NNC control, based upon information provide by the PTOS's ambient light sensors and IMCCD. Under bright lighting conditions, a higher current will be induced in the MMRI PiN configuration by ambient light, and will offset a modulated lower MMRI NiP current. This produces a net perception of light. Because images in the normal environment have constantly changing light and dark qualities, implant will also rapidly change their electrical outputs between "light currents" and "dark currents". Modulation of the implant "light current" can also be performed by the AIRES PTOS by projecting additional visible light images, superimposed over the ambient light images.

During operation, AIRES uses its NNC to process digitized images provided by its IMCCD. In the preferred embodiment, AIRES projects superimposed, real-time-video, visible and infrared images onto the retinal implants. These images may be displayed either simultaneously or in rapid succession from the IRVCRT. Alternatively, any appropriate display device such as a filtered active matrix LCD, LED display, or filtered plasma display may be used to produce the visible and IR light and images. AIRES controls the PTOS projected images by changing their wavelengths, intensity, duration, and pulse frequency. A patient input device (e.g. an Input Stylus Pad) is also interfaced with the NNC and allows the patient to modify the IR and visible-light images produced by the PTOS headset. This patient "feedback" is analyzed by the AIRES NNC, then compared with the computer processed images from the IMCCD, and the differences learned by the AIRES Neuro-Net software. After a teaching period, the NNC is able to automatically adjust the computer generated visible and IR images to improve image quality without assistance by the patient. By adjusting the stimulating frequency and duration of the PTOS IR and visible images, AIRES will also be able to stimulate the sensation of color in some patients. This is in a manner similar to color sensations induced in normal sighted persons, by using a spinning black-and-white Benham top, or by using frequency modulated black and white television monitors.

The MMRI and AIRES components of this invention differ from the previous art primarily in the following ways. Visible and infrared images and light are used to selectively modulate MMRI function. A MMRI can be stimulated with light from either of its two photoactive sides and produce localized stimulating electric current from both sides. The flattened shapes of the MMRIs allow preferential orientation of the devices toward incident light when disposed in the subretinal space. Using the AIRES system, electrical output from MMRIs can be programmed for individual patient needs. The design of the MMRIs also allows the alternative to use them to stimulate the nerve fiber layer, ganglion cell layer, or inner plexiform layer of retina from vitreous body side; or to use them to stimulate the remnant photoreceptor layer, bipolar cell layer, or the inner plexiform layer from the subretinal space, by reversing their polarities during fabrication. The biphasic nature of the electrical current output from MMRIs are also better tolerated biologically than the mostly monophasic nature of electrical stimulation of the previous art.

DETAILED DESCRIPTION OF THE PRESENTLY PREFERRED EMBODIMENTS

Figure 1:
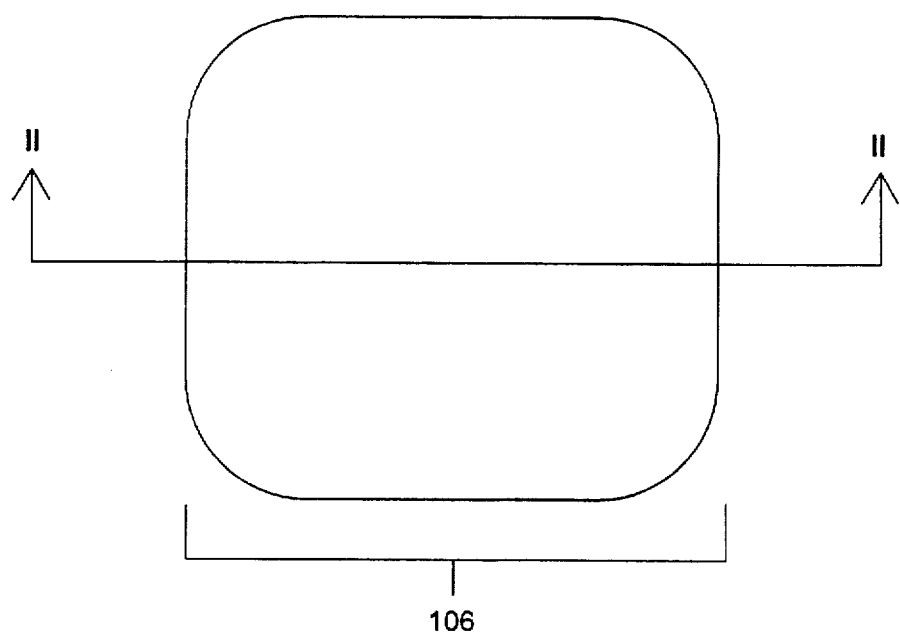
FIG. 1 is a plan view of one embodiment of the microphotodiode retinal implant of this invention (MMRI)

In a preferred embodiment of this invention (FIGS. 1–2), each microphotodiode implant (106) is fabricated as a flattened cubic device (hereafter MMRI) containing a single two-side microphotodiode. In this preferred embodiment, each MMRI (106) forms the shape of a flattened cube with rounded corners and edges, and is sized in microscopic dimensions, and is a physically independent unit. MMRIs (106) may function as a PiN or NiP device, depending upon which of its two photosensitive sides, the P-side (107a) or the N-side (107b) is stimulated by visible and/or infrared light (108). From top to bottom, the layers of the MMRI (106) include the P electrode (110) preferably made of P doped polysilicon, a multilayer dielectric filter (122) to allow passage of only visible light (400 nm to 740 nm) to the next P+ layer (112), a contact pad (114) fabricated from any or all or compounds of the following: gold, aluminum, titanium, and chromium, to establish electrical contact between layers (110) and (112), an intrinsic layer (126) which forms naturally between the P+ layer (112) and the N-type silicon substrate (128), a N+ layer (118), a multilayer dielectric filter (124) to allow passage of only infrared light (740 nm to 900 nm) to the N+ layer (118), a contact pad (120) fabricated from any or all compounds of the following: gold, aluminum, titanium, and chromium to establish electrical contact between the N+ layer (118) and the last layer that is the N electrode (116), preferably made of N-doped polysilicon.

Figure 2:
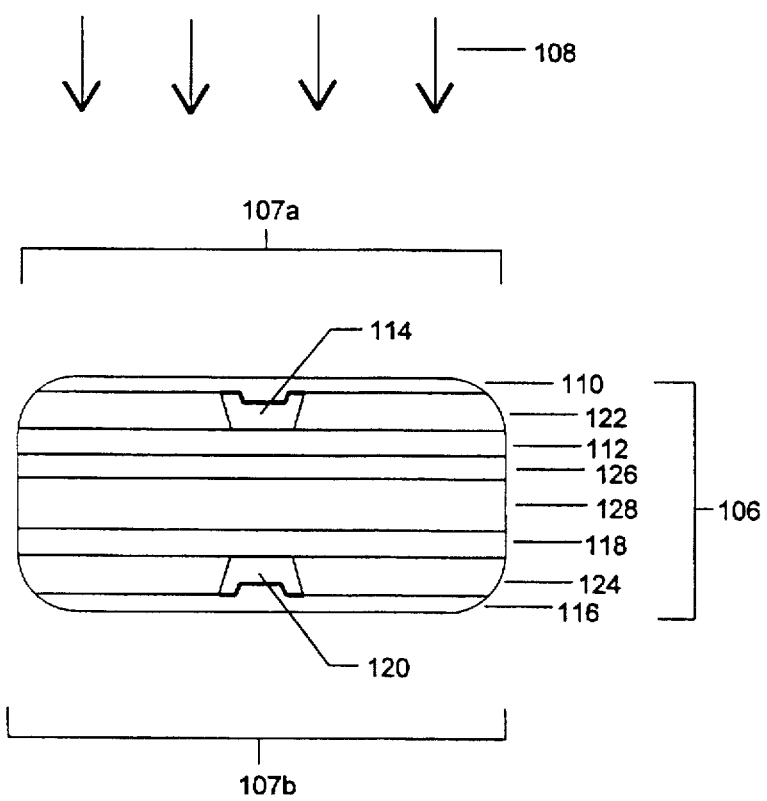
FIG. 2 is a cross-section taken along the plane of the line II—II of FIG. 1.

Although FIGS. 1–2 shows that the P electrode (110) and the N electrode (116) cover the entire surface of the MMRI (106), in alternate embodiments, the P electrode (110) may cover a fraction of the photosensitive side P-side (107a), and the N electrode (116) may cover a fraction of the photosensitive side N-side (107b). These fractions may range from 0.1% to 99.9%. The purpose of fractional coverage of the P electrode (110) and N electrode (116) is to allow concentration of electric currents produced by the MMRI (106). Also as shown in FIGS. 1–2, the width and depth of the MMRI (106) are the same dimensions and may vary between 5 µm and 100 µm, and the height is 25% to 50% that of the width and depth. However, in alternate embodiments, MMRIs (106) may be manufactured as small as 1 μm and as large as 2000 μm in depth and width, and the width and depth need not be the same; and the height of the MMRI may be from 1% to 500% of the width and depth. Preferably, the MMRI N-type silicon substrate (128) has an ohmic restive value between 50 and 2000 ohm-cm². However, in alternate embodiments, the MMRI N-type substrate (128) may have ohmic resistive values of between 1 ohm-cm² and 100,000 ohm-cm². The designed and preferred electric current output of each MMRI (106) is on the order of 1 to 5000 nA depending on incident lighting (108). Nevertheless, a range of 0.01 nA to 200,000 nA is also suitable.

Figure 3:
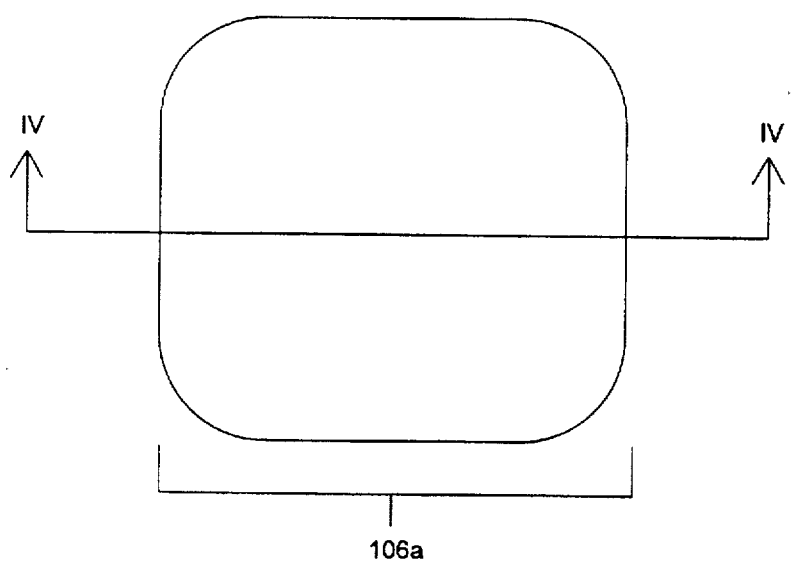
FIG. 3 is a plan view of a second embodiment of this invention (MMRI-E)
Figure 4:
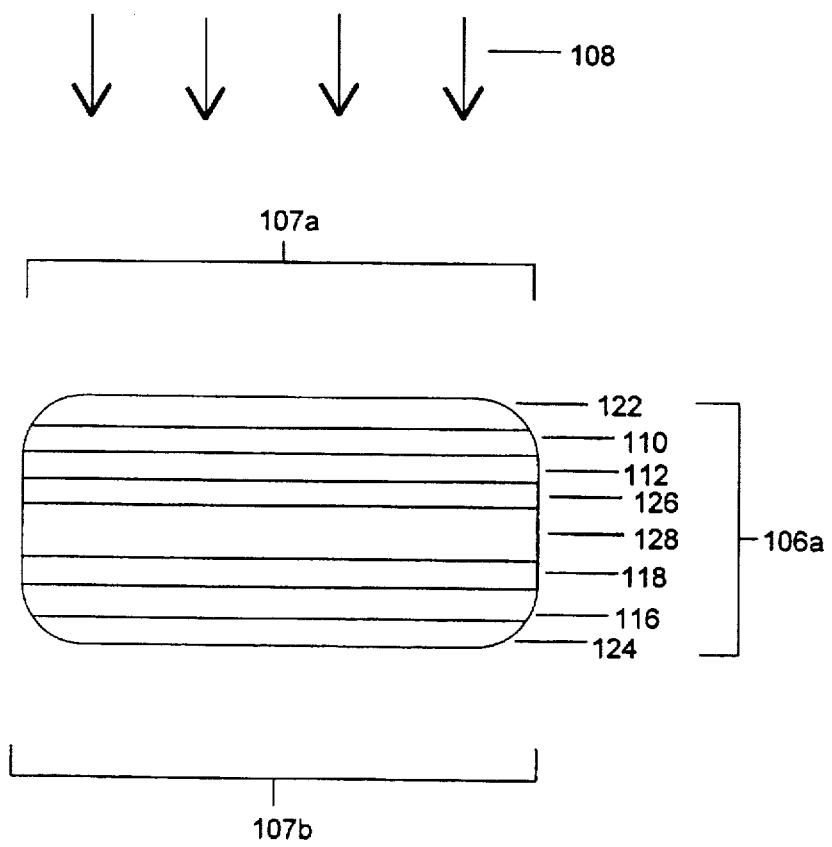
FIG. 4 is a cross-section taken along the plane of the line IV—IV of FIG. 3.

In a second embodiment of this invention (MMRI-E) (FIGS. 3–4), the MMRIs of FIGS. 1–2 are fabricated so that the polysilicon layer 110 is sandwiched between the multi-layer dielectric visible light filter layer 122 and the P+ layer 112, and the polysilicon layer 116 is sandwiched between the multi-layer dielectric IR filter layer 124 and the N+ layer 124. The aluminum contact pads 114 and 120 of FIGS. 1–2 are not needed in this embodiment. This embodiment results in MMRI-Es which predominately stimulate retinal cells adjacent to the MMRI-Es rather than on top of the MMRI-Es. This second embodiment is used in those patients where side simulation will induce better vision than top stimulation. The remaining layers of the intrinsic layer 126, and the N-type silicon substrate layer 128, the P-side 107a, and the N-side 107b are unchanged.

Figure 5:
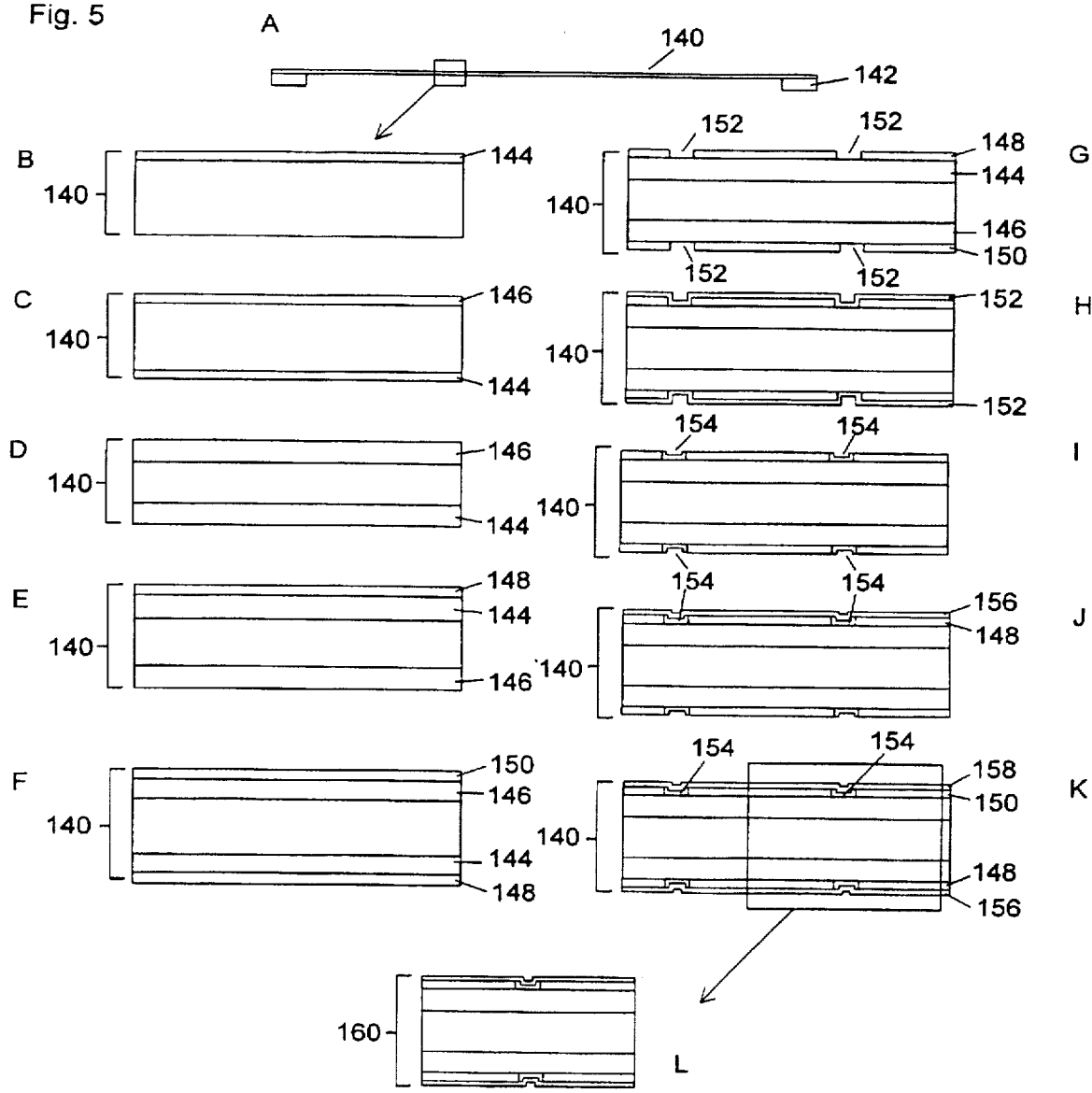
FIG. 5 shows the manufacturing process of the microphotodiode retinal implant of FIG. 1 (MMRI)

FIG. 5, A through L illustrates the manufacturing steps of the preferred MMRIs. As shown in FIG. 5A, a 3" float zone 1-0-0 N-type silicon wafer (140) at 200 to 400 ohm-cm is thinned to 8 μm, and a silicon support ring (142) 0.4" to 0.5" wide (prepared by chemical etch and channel stop techniques to have 30–40 degree i.d. taper) is then oxide bonded to target wafer (140). As shown in FIG. 5B, P+ layer (144) is ion implanted to 0.2 μm depth on one side of the wafer (140). The other side is masked from the implantation. As shown in FIG. 5C, wafer (140) is flipped over and the N+ layer (146) is ion implanted to 0.2 μm depth on the second side. The first P+ side (144) is masked from implantation.

As shown in FIG. 5D, both the P+ (144) and N+ (146) layers are thermally driven to 0.5 μm to 0.6 μm depth. As shown in 5E, Multiple alternating layers of TiO₂ and quartz are evaporation deposited to produce an interference filter (148) to pass 400–740 nm visible light, but stops 740–900 nm IR light on the P+ side (144). The total thickness of this dielectric layer (148) is about 3.5 to 5 μm. As shown in FIG. 5F, the wafer is flipped over to expose the N+ side (146) and multiple alternating layers of TiO₂ are evaporation deposited to produce a interference filter (150) which passes 740–900 nm IR light, but stops 400–740 nm visible light on the N+ side (146). Total thickness of this dielectric layer (150) is about 2–3 μm. In FIG. 5G, photoresist is spun-on and both sides of the wafer (140) are patterned with 8 μm×8 μm contact holes (152) which penetrate the interference films (148 and 150) to the P+ layer (144) and the N+ layer (146), with hole spacing of 50 μm in a square grid fashion. As shown in FIG. 5H, 1.0 μm of aluminum (152) is deposited to both sides of the wafer (140). In FIG. 5I, photoresist is spun-on and both sides of the wafer (140) are patterned to leave 12 μm×12 μm aluminum contact pads (154) over all the 8 μm×8 μm contact holes, and then thermally drive in the aluminum. In FIG. 5J, plasma assisted, low pressure, chemical vapor deposition is used to deposit 0.2 μm to 0.5 μm of P+ polysilicon (156) on the P+ side interference filter (148) of the wafer (140) to establish electrical contact with the aluminum contact pads (154), at 250°–300° C. The other side of wafer is masked. In FIG. 5K, plasma assist, low pressure, chemical vapor is used to deposit 0.2 μm to 0.5 μm of N+ polysilicon (158) on N+ side interference filter (150) of the wafer (140) to establish electrical contact with the aluminum contact pads (154), at 250°–300° C. The other side of wafer is masked. In FIG. 5L, the 3 inch wafer is eximer laser cut into 50 μm×50 μm squares (160) with one contact pad centered on each side of every square. The final cleaned, washed, and recovered squares are MMRIs. The MMRIs may be briefly tumbled in a glass container using ultrasonic energy to slightly round off the sharp corners and edges of the devices.

Figure 6:
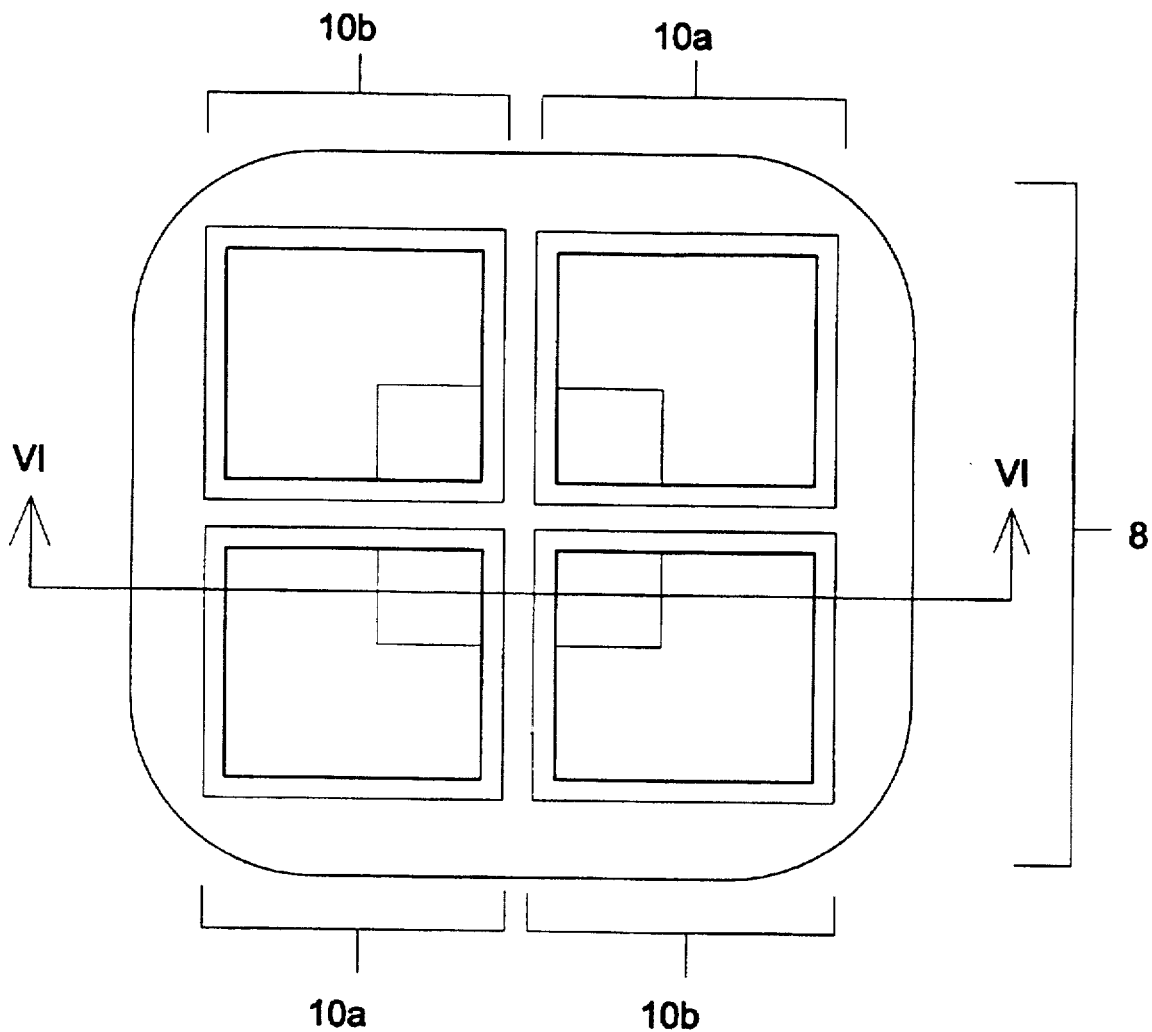
FIG. 6 is a plan view of a third embodiment of this invention (MMRI-4), which is composed of two pairs of MMRI subunits.
Figure 7:
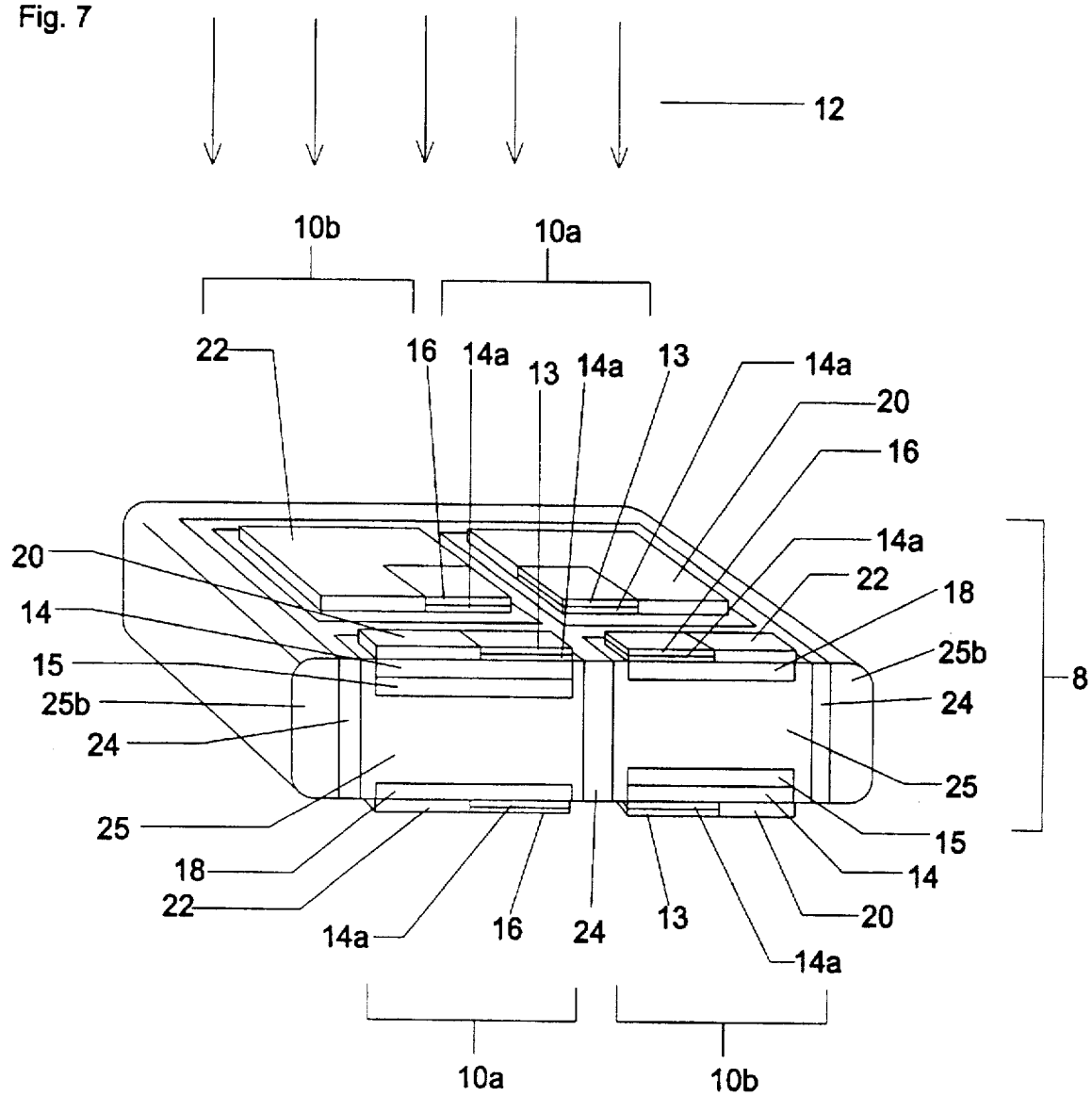
FIG. 7 is a perspective view in cross-section taken along the plane of line VI—VI of FIG. 6.

FIGS. 6–7 illustrate the layered microarchitecture of a third embodiment of the artificial retina device of this invention, designated at (8), and is referred to for convenience as a MMRI-4 to distinguish it from other embodiments of this invention. MMRI-4 (8) forms the shape of a flattened cube with rounded corners and edges, and is sized in microscopic dimensions. It is comprised of four microphotodiode subunits (10a×2 and 10b×2). Each microphotodiode subunit (10a or 10b) of the MMRI-4 (8) may be a PiN or NiP device, depending upon which of its photosensitive surfaces is oriented toward light (12). For example, as shown in FIG. 7, the near left microphotodiode (10a) is behaving as a PiN subunit, because the P+ tub (14) is facing incident light (12). In contrast, the near right microphotodiode (10b) is behaving as a NiP subunit because its N+ tub (18) is facing incident light (12). It can be readily appreciated, that if the MMRI-4 (8) is flipped over, the microphotodiode subunit (10a) will have its N+ tub (18) facing incident light and will therefore behave as a NiP device. Similarly, when flipped over, the microphotodiode subunit (10b) will have a P tub (14) facing incident light and will behave as a PiN device.

Further illustrated in FIGS. 6–7, the MMRI-4 (8) in its basic form contains four positive (P) electrodes (13) disposed on the four P+ tub (14) surfaces on the top and bottom sides of the MMRI-4 (8) (note the bottom structure of the two rear microphotodiode subunits cannot be seen in FIG. 7). The P electrodes (13) are preferably made of P doped polysilicon, produced by chemical vapor deposition, and are deposited on the inner corners of the P+ tubs (14). Interposed between the P electrodes (13) and the P+ tubs (14), is a layer of gold, titanium or chromium (14a) to promote adhesion and to act as a light block. The MMRI-4 (8) also contains four negative (N) electrodes (16) disposed on the four N+ tub (18) surfaces. The N electrodes (16) are preferably made of N-doped polysilicon, produced by chemical vapor deposition, and are deposited on the inner corners of the N+ tubs (18). Interposed between the N electrodes (16) and the N+ tubs (18) is also a layer of gold, titanium or chromium (14a) to promote adhesion and to act as a light block.

Alternatively, the P electrodes (13), and N electrodes (16) may be constructed of any suitable material that will conduct electric current. These conductive materials may include, but are not limited to, gold, chromium, aluminum, iridium, and platinum or any combination or compounds made from these materials. The P electrodes (13) and the N electrodes (16) may cover any fraction, from 0.1% to 99.9%, of their respective P+ tub (14) or N+ tub (18) surfaces. Filter layers (20) are disposed on the portion of the P+ tub (14) surfaces not covered by the P electrodes (13). These filter layers (20) are preferably fabricated from multi-layer dielectric coatings and allow passage of only visible light (400 nm to 740 nm) to the P+ tub (14) surfaces. Filter layers (22) are disposed on the N+ tub (18) surfaces not covered by the N electrodes (16). These filter layers (22), are also preferably fabricated from multi-layer dielectric coatings and allow passage of only infrared light (740 to 900 nm) to the N+ tub (18) surfaces. Under each P+ tub (14), an intrinsic layer (15) forms naturally between the P+ tub (14) and the N-type silicon substrate (25). The N+ tub layers (18) are created by ion implantation of additional N-type phosphorus into the N-type silicon substrate (25). Ion implantation of P-type boron around each MMRI-4 subunit (10a×2, 10b×2) produces a channel stop (24) to electrically separate the microphotodiode subunits from each other. Outside the channel stop material (24) is surrounding N-type silicon substrate (25b).

In the embodiment of the invention shown in FIGS. 6–7, the width and depth of the MMRI-4 (8) are the same dimensions and are between 10 and 50 microns, and the height is 25% to 50% that of the width and depth. This flattened cubic configuration will allow one or the other of the two flattened photoactive sides of the MMRI-4 (8) to be preferentially directed to incident light (12), when the MMRI-4 (8) is implanted in the subretinal space. MMRI-4s (8) may be manufactured as small as 1 micron and as large as 1000 microns in depth and width, and the width and depth need not be the same; further the height of the MMRI-4 may be from 1% to 500% of the width and depth. In the embodiment of FIGS. 6–7, the MMRI-4 N type substrate (25 and 25b) has an ohmic resistive value between 50 and 2000 ohm-cm$^2$. However, the MMRI-4 N-type substrate (25 and 25b) may have ohmic resistive values of between 1 ohm-cm$^2$ and 100,000 ohm-cm$^2$. The designed and preferred electric current output of each MMRI-4 subunit microphotodiode (10a or 10b) is on the order of 1 to 5000 nA depending on incident lighting (12). Nevertheless, a range of 0.01 nA to 200,000 nA may also be suitable. The MMRI-4 (8) may also be modified to achieve greater or lesser electrical output by changing the area of each P electrode (13), and/or the N electrode (16) relative to the area of their respective P+ tub (14) and N+ tub (18).

Figure 8:
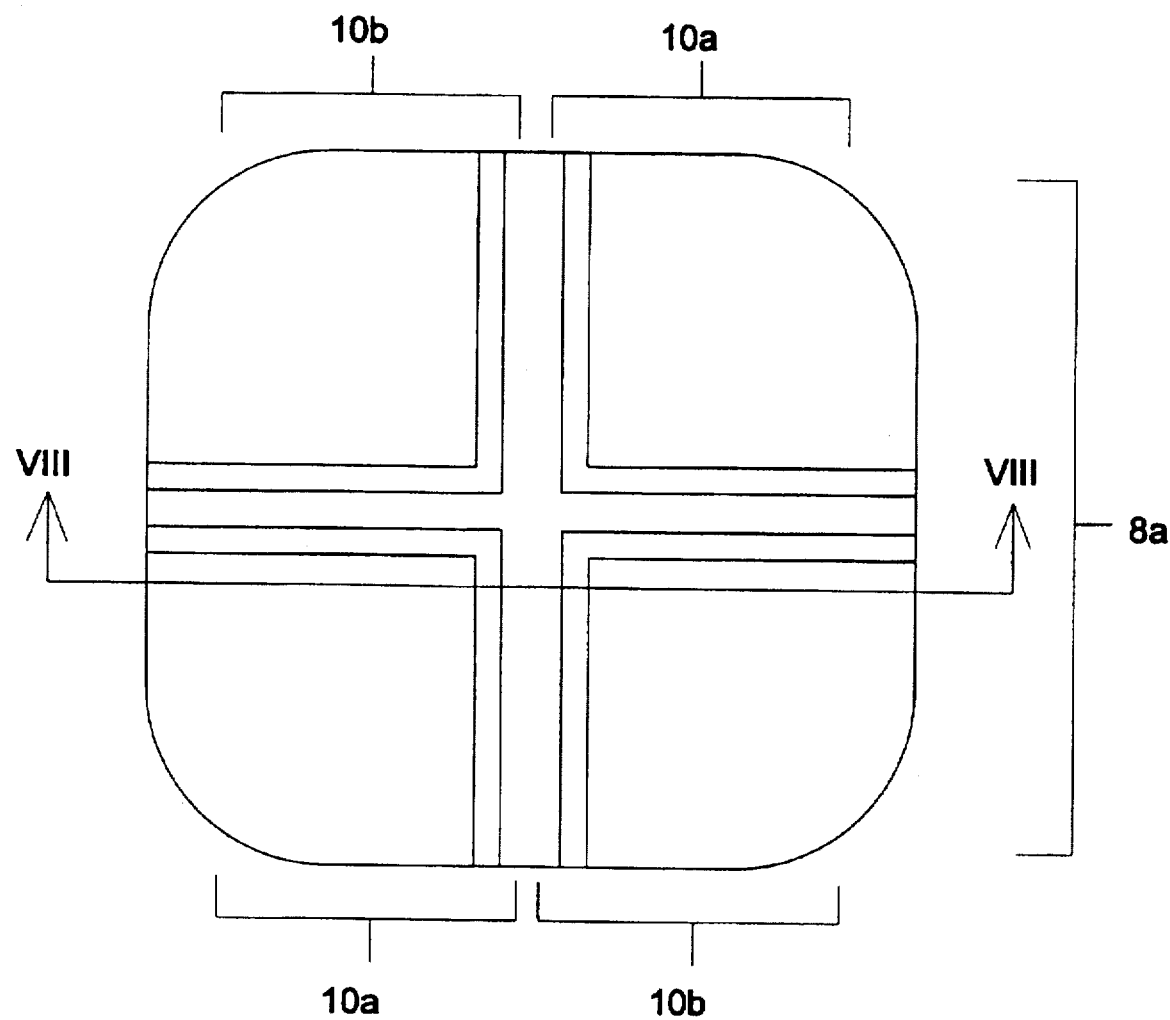
FIG. 8 is a plan view of a fourth embodiment of this invention (MMRI-4E), which is composed of two pairs of MMRI-E subunits.
Figure 9:
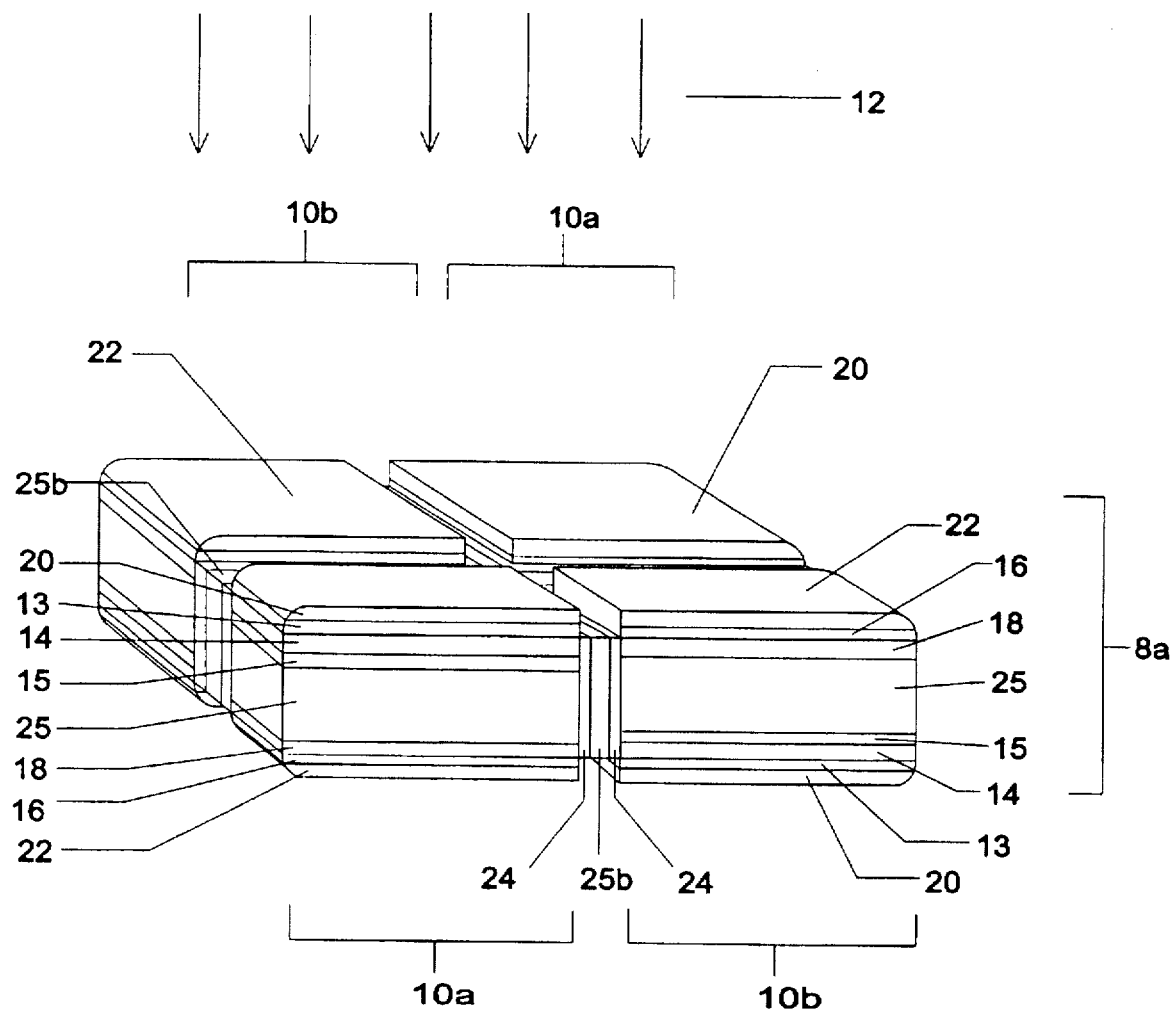
FIG. 9 is a perspective view in cross-section taken along the plane of line VIII—VIII of FIG. 8.

FIGS. 8–9 illustrate the layered microarchitecture of a fourth embodiment of the artificial retina device of this invention, designated at (8a), and is referred to for convenience as a MMRI-4E to distinguish it from other embodiments of this invention. MMRI-4E (8a) forms the shape of a flattened cube with rounded corners and edges, and is sized in microscopic dimensions. It is comprised of four microphotodiode subunits (10a×2 and 10b×2). Each microphotodiode subunit (10a or 10b) of the MMRI-4E (8a) may be a PiN or NiP device, depending upon which of its photosensitive surfaces is oriented toward light (12). For example, as shown in FIG. 9, the near left microphotodiode (10a) is behaving as a PiN subunit, because the P+ tub (14) is facing incident light (12). In contrast, the near right microphotodiode (10b) is behaving as a NiP subunit because its N+ tub (18) is facing incident light (12). It can be readily appreciated, that if the MMRI-4E (8a) is flipped over, the microphotodiode subunit (10a) will have its N+ tub (18) facing incident light and will therefore behave as a NiP device. Similarly, when flipped over, the microphotodiode subunit (10b) will have a P tub (14) facing incident light and will behave as a PiN device.

Further illustrated in FIGS. 8–9, the MMRI-4E (8a) in its basic form contains four transparent positive (P) electrodes (13) disposed on the four P+ tub (14) surfaces on the top and bottom sides of the MMRI-4E (8a) (note the bottom structure of the two rear microphotodiode subunits cannot be seen in FIG. 9). The transparent P electrodes (13) are preferably made of P doped polysilicon, produced by chemical vapor deposition, and are deposited on the P+ tubs (14).

The MMRI-4E (8a) also contains four transparent negative (N) electrodes (16) disposed on the four N+ tub (18) surfaces. The transparent N electrodes (16) are preferably made of N-doped polysilicon, produced by chemical vapor deposition, and are deposited on the N+ tubs (18).

Alternatively, the P electrodes (13), and N electrodes (16) may be constructed of any suitable material that can be deposited in a thin transparent layer, and that will conduct electric current. These conductive materials may include, but are not limited to, gold, chromium, aluminum, iridium, and platinum or any combination or compounds made from these materials. Filter layers (20) are disposed on the P electrodes (13). These filter layers (20) are preferably fabricated from multi-layer dielectric coatings and allow passage of only visible light (400 nm to 740 nm) through to the transparent P electrodes (13) and then to the P+ tub (14) surfaces. Filter layers (22) are disposed on the N+ tub (18) surfaces. These filter layers (22), are also preferably fabricated from multi-layer dielectric coatings and allow passage of only infrared light (740 to 900 nm) through to the transparent N electrodes (16) and then to the N+ tub (18) surfaces. Under each P+ tub (14), an intrinsic layer (15) forms naturally between the P+ tub (14) and the N-type silicon substrate (25). The N+ tub layers (18) are created by ion implantation of additional N-type phosphorus into the N-type silicon substrate (25). Ion implantation of P-type boron around each MMRI-4 subunit (10a×2, 10b×2) produces a channel stop (24) to electrically separate the microphotodiode subunits from each other. Outside the channel stop material (24) is surrounding N-type silicon substrate (25b).

In the embodiment of the invention shown in FIGS. 8–9, the width and depth of the MMRI-4E (8a) are the same dimensions and are between 10 and 50 microns, and the height is 25% to 50% that of the width and depth. This flattened cubic configuration will allow one or the other of the two flattened photoactive sides of the MMRI-4E (8a) to be preferentially directed to incident light (12), when the MMRI-4E (8a) is implanted in the subretinal space. MMRI-4Es (8a) may be manufactured as small as 1 micron and as large as 1000 microns in depth and width, and the width and depth need not be the same; further the height of the MMRI-4E may be from 1% to 500% of the width and depth. In the embodiment of FIGS. 8–9, the MMRI-4E N type substrate (25 and 25b) has an ohmic resistive value between 50 and 2000 ohm-cm$^2$. However, the MMRI-4E N-type substrate (25 and 25b) may have ohmic resistive values of between 1 ohm-cm$^2$ and 100,000 ohm-cm$^2$. The designed and preferred electric current output of each MMRI-4E subunit microphotodiode (10a or 10b) is on the order of 1 to 5000 nA depending on incident lighting (12). Nevertheless, a range of 0.01 nA to 200,000 nA may also be suitable. The MMRI-4E (8a) may also be modified to achieve greater or lesser electrical output by changing the thickness and therefore the transparency of each P electrode (13), and/or the N electrode (16).

Figure 10:
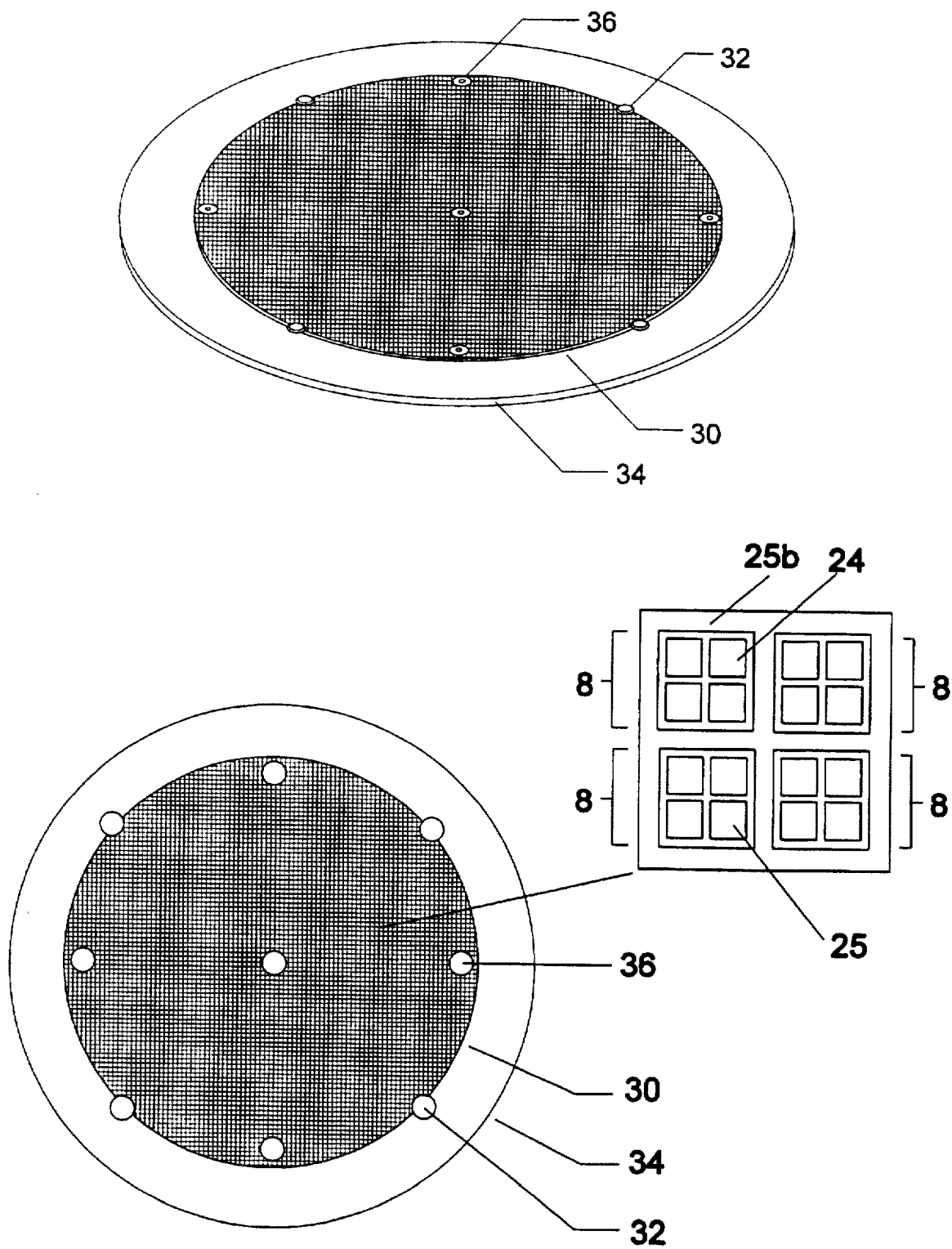
FIG. 10 shows three dimensional and plan views, and a magnified inset view of a 3 inch silicon wafer secured onto a thicker 4 inch silicon wafer during the manufacture of the microphotodiode retinal implants (MMRI-4) of FIG. 6.

In FIG. 10, and FIG. 10 inset, the manufacture of the preferred MMRI-4s (8) is illustrated. The first stage in the manufacture of MMRI-4s begins with a three-inch diameter N type 1-0-0 silicon wafer (30) that is 8 microns thick. This wafer (30) is secured around its circumference to a four-inch wafer (34) approximately 500 microns thick, with titanium pins (32). As shown in the FIG. 4 inset, a plurality of N-type square island groups (8) that eventually become the MMRI-4s are isolated from the surrounding N-type substrate (25b) by ion implantation of P-type boron channel stops (24) from both sides. The channel stops (24) are heat driven through the entire thickness of the three-inch diameter wafer (30) to isolate four square columns of N-type silicon substrate (25) per square island (8). Each square column (25) is 11 microns per side and separated from adjacent square columns (25) of the same MMRI-4 (8) by 1 micron of P-type silicon channel stop (24). The resultant square islands (8), including the channel stops (24) are 21 microns per side. The square islands (8) are separated from each other by 1 micron of N-type silicon substrate (25b). Alignment holes (36) are excimer laser drilled through the three-inch wafer (30). These holes (36) facilitate alignment of fabrication masks from either side of the three-inch wafer (30).

The P+ tubs (14) shown in FIG. 7 are created by ion implantation and thermal diffusion of P-type boron into the N-type substrate square columns (25). Two P+ tubs (14) are formed on each side of the MMRI-4 square island (8) and are arranged diagonally to each other. Intrinsic layers (15) automatically form between the P+ tubs (14) and the N type silicon substrate of the square columns (25). The N+ tubs (18) are created by ion implantation and thermal diffusion of additional N-type phosphorus into the N-type silicon substrate square columns (25) from the opposite side of the P+ tubs (14). After deposition of a gold, chromium or titanium layer (14a) to improve adhesion and to act as a light block on the inner corners of all the P+ tubs (14) and N+ tubs (18), P-doped polysilicon electrodes (13) and the N-doped polysilicon electrodes (16), each covering 10% of the P+ tub (14) and N+ tub (18) surfaces are then deposited on their respective P+ tubs (14) and N+ tubs (18). The three-inch wafer (30), still secured on the four-inch support wafer (34), of FIG. 10 is then transferred to a vacuum deposition chamber where multilayer dielectric coatings (20), that bandwidth pass visible light (400-740 nm) are deposited on the P+ tubs (14) and multilayer dielectric coatings (22) that bandwidth pass infrared light are deposited on the N+ tubs (18). The three-inch wafer (30) is then flipped over and re-secured on the four-inch support wafer (34). Again, multilayer dielectric coatings (20) that bandwidth pass visible light (400 to 740 nm), and multilayer dielectric coatings (22) that bandwidth pass infrared light (740 to 900 nm) are deposited on their respective P+ tubs (14) and the N+ tubs (18) after deposition of the gold, chromium or titanium adhesion and light block layer (14a).

As shown in FIG. 10, the final three-inch wafer (30), with fabricated MMRI-4 square islands (8), is then removed from the four-inch support wafer (34). The three-inch wafer (30) is then rebonded to the four-inch wafer (34) with an aqueous dissolvable adhesive. Using an excimer laser, X and Y direction cuts are made to separate the MMRI-4 islands (8) from each other. The MMRI-4 islands (8), however, still remain bonded to the support wafer (34) by adhesive. The wafer assembly (30 and 34) is then placed in an aqueous solution solvent to dissolve the adhesive. The MMRI-4 square islands (8) are recover from the aqueous solution using standard filtering techniques, and are washed, and dried. The recovered MMRI-4 islands (8) are briefly tumbled in a glass container using ultrasonic energy. This tumbling process will slightly round off the sharp corners and edges of the MMRI-4s (8). The final devices, demonstrated by the MMRI-4s (8) of FIG. 7, are then washed again, recovered, sterilized, and then placed in a biologically compatible semi-solid or liquid vehicle for implantation into the eye.

Figure 11:
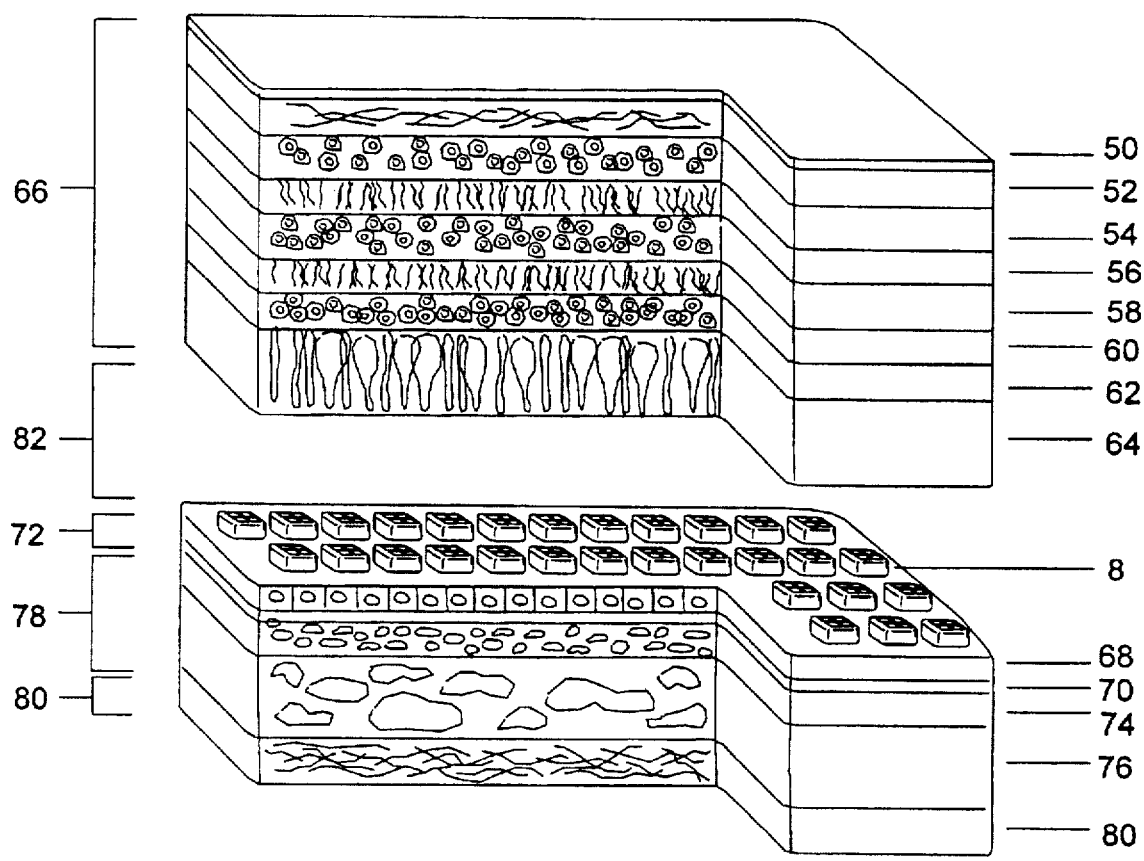
FIG. 11 shows the microphotodioce retinal implants (MMRI-4) of FIG. 6 implanted in the preferred location of the subretinal space.

FIG. 11 shows MMRI-4s (8) implanted in their preferred monolayer position in the subretinal space (82). The layers of the eye at the posterior pole from inside the eye to outside the eye are shown in their respective positions: internal limiting membrane (50); nerve fiber layer (52); ganglion and cell layer (54); inner plexiform layer (56); inner nuclear layer (58); outer plexiform layer (60); outer nuclear cell layer (62); and photoreceptor layer (64), all of which constitute the inner retinal layer (66). The MMRI-4s (8) are disposed between the inner retinal layer (66), and the retinal pigment epithelium (68) and Bruch's membrane (70), which together constitute the outer retinal layer (72). External to the outer retinal layer (72) are the choriocapillaris (74) and choroid (76) which comprise the choroidal vasculature (78), and sclera (80), which comprised the outer coat of the eye.

Figure 12:
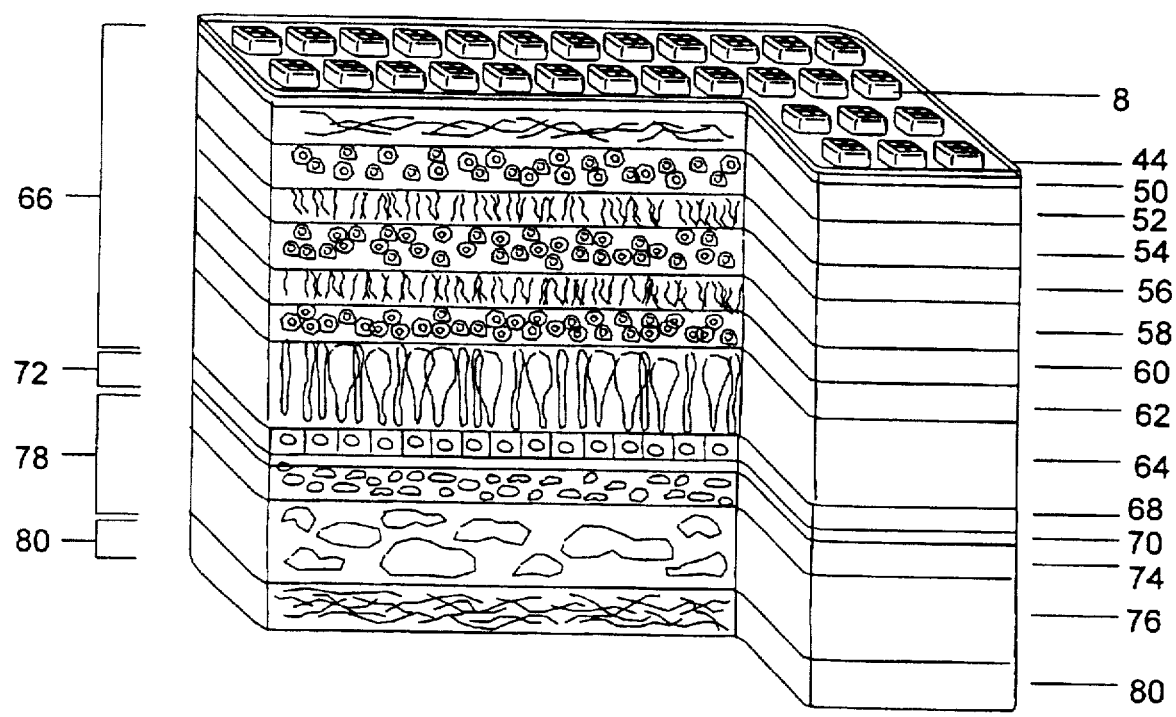
FIG. 12 shows the microphotodiode retinal implants (MMRI-4) of FIG. 6 implanted in an alternate location, on the nerve fiber layer surface of the retina.

FIG. 12 shows MMRI-4s (8) in an alternate embodiment location, positioned on the internal limiting membrane surface (50) of the retina and close to the nerve fiber layer (52). In this location, MMRI-4s (8) are embedded into a flexible, biologically compatible sheet (44), that allows both of the flattened photoactive surfaces of each MMRI-4s (8) to be exposed. Electrical stimulation of the retinal nerve fiber layer (52), through the internal limiting membrane surface (50) by the MMRI-4s (8) will also induce artificial vision, but the quality of images produced will not be as well formed as from stimulation of the retina from the subretinal space ((82) as shown in FIG. 11. The layers of the eye at the posterior pole from inside the eye to outside the eye, shown in their respective positions in FIG. 12, are: internal limiting membrane (50); nerve fiber layer (52); ganglion cell layer (54); inner plexiform layer (56); inner nuclear layer (58); outer plexiform layer (60); outer nuclear layer (62); and photoreceptor layer (64), all of which constitute the inner retinal layer (66). The retinal pigment epithelium (68) and Bruch's membrane (70), together constitute the outer retinal layer (72). External to the outer retinal layer (72), choriocapillaris (74) and choroid (76) comprise the choroidal vasculature (78), and sclera (80), the outer coat of the eye.

As illustrated in FIGS. 13–16, in a further embodiment of the MMRI component of this invention, the two dielectric filter layers embedded in each MMRI will be both of the visible light transmitting type (210, 222), or will be both of the IR light transmitting type (310, 322). Instead of using polysilicon for their electrodes, the electrodes of these devices (202, 204, 302, 304) may be fabricated from gold, although aluminum or platinum may also be used, and will be deposited with an industry standard "wafer bumping" process. This will form each electrode into a projecting-like structure bonded to an aluminum contact pad (214, 224, 314, 324). Each gold projecting electrode (202, 204, 302, 304) will be then covered over its entire surface, with the exception of the tip, by an insulating layer of silicon dioxide (208, 226, 308, 326) or alternatively silicon nitrite. The height of the projecting electrode will be higher on one side of the device than on the other side, and may be 5 µm to 200 µm on the higher side (202, 302) and 1 µm to 195 µm on the lower side (204, 304). When thus fabricated, these individual devices are will form two populations: 1) a visible light responsive device (MMRI-IPV) designated at (200) with a higher projecting electrode (HPE) (202) on the negative (N) side (205b), and a lower projecting electrode (LPE) (204) on the positive (P) side (205a), and 2) a IR light responsive device (MMRI-IPIR) designated at (300) with a HPE (302) on the P side (305b) and a LPE (304) on the N side (305a).

Figure 17:
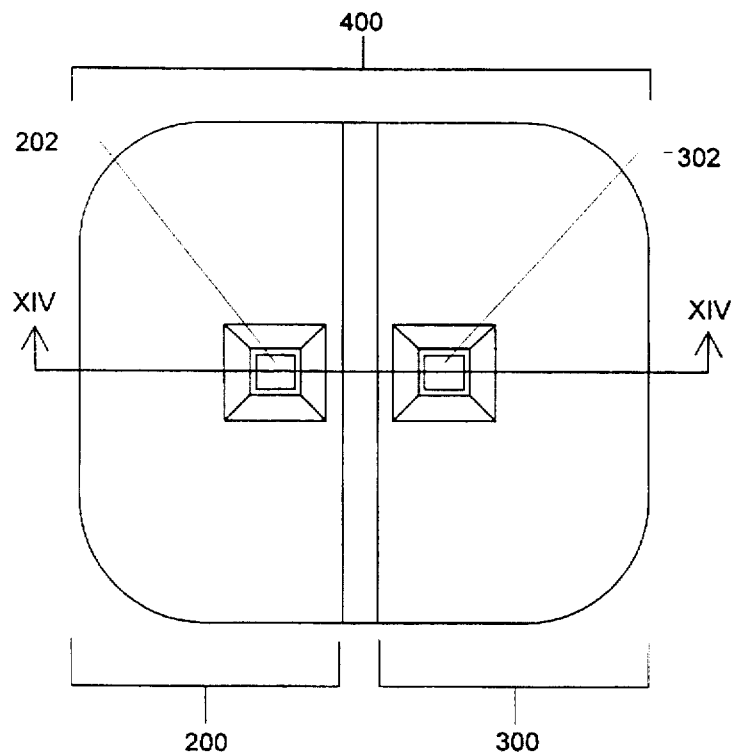
FIG. 17 shows a plan view of a seventh embodiment of the microphotodiode implant of this invention (MMRI-IPVIR-A)
Figure 18:
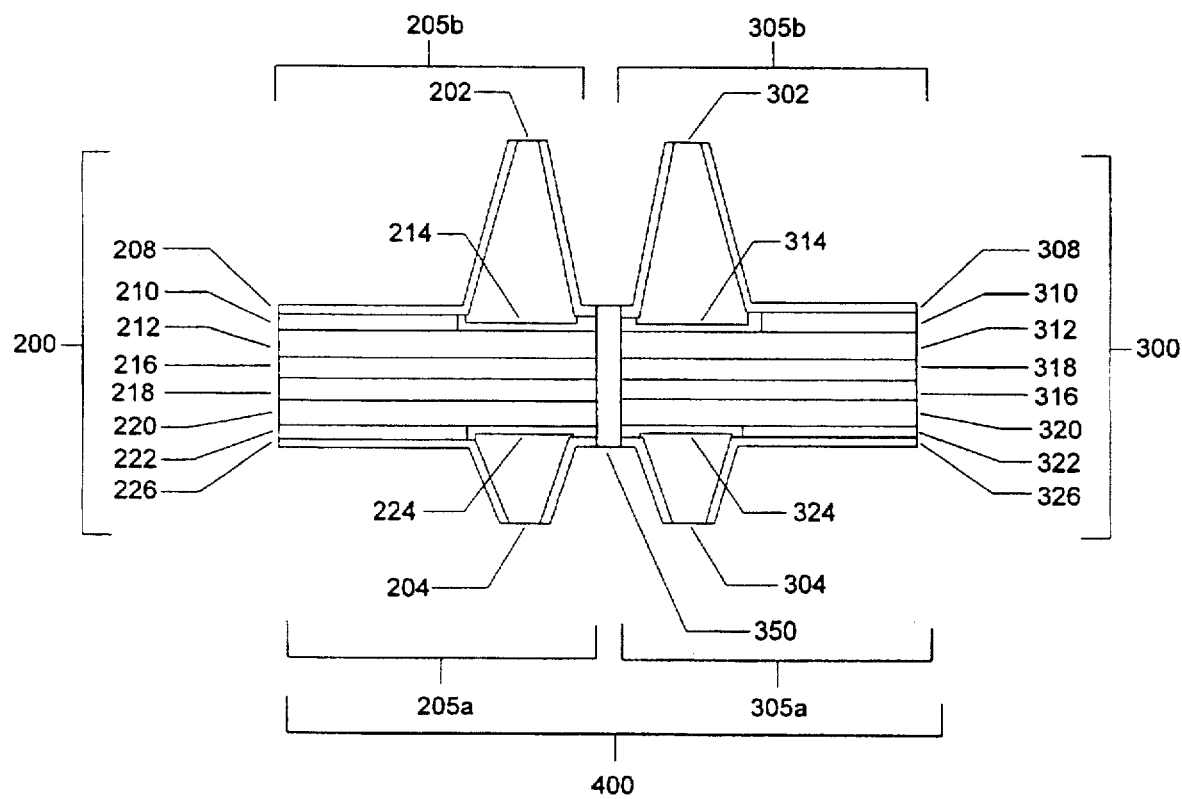
FIG. 18 is a cross-section taken along the plane of line XIV—XIV of FIG. 17.

As illustrated in FIGS. 17–18, the two units, MMRI-IPV (200) and MMRI-IPIR (300), can also exist as a combination unit (MMRI-IPVIR-A) designated at (400), comprised of one MMRI-IPV (200) and one MMRI-IPIR (300). The HPE (202) of the MMRI-IPV (200) and the HPE (302) MMRI-IPIR (300) will be pointed in the same direction on the one side of the MMRI-IPVIR-A. The LPE (204) of the MMRI-IPV (200) and the LPE (304) of the MMRI-IPIR (300) will be also pointed together in the same direction, but on the opposite side of the MMRI-IPVIR-A (400) and in a direction opposite the direction of the HPEs (202, 302).

Figure 21:
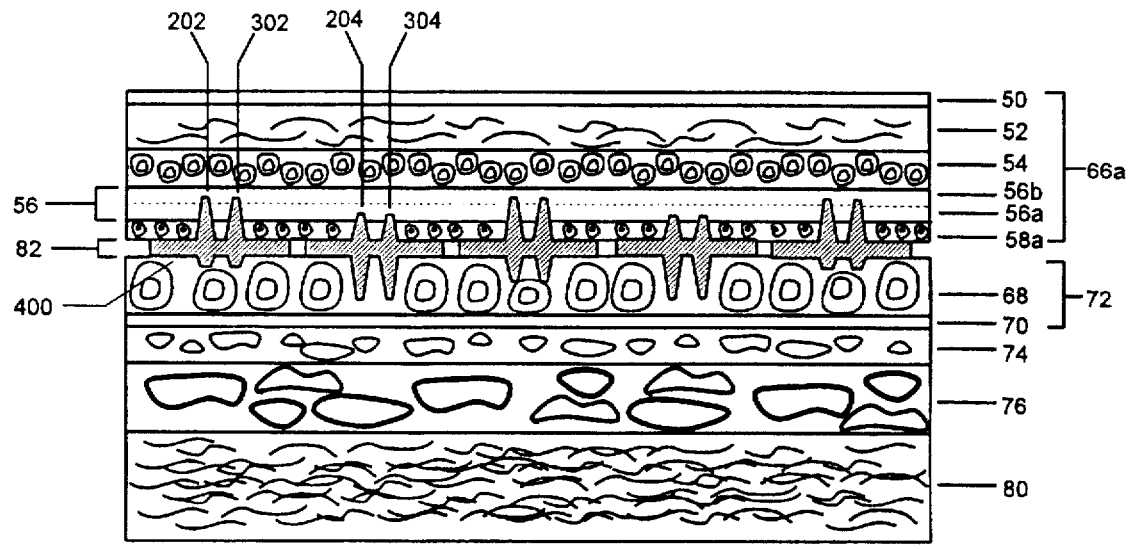
FIG. 21 is a cross-section of the retina showing the microphotodiode implants of FIG. 17 (MMRI-IPVIR-A) in their preferred location in the subretinal space, with their electrodes penetrating into the sublamina B, and sublamina A locations of the inner plexiform.

As illustrated in FIG. 21, the MMRI-IPVIR-A (400) are disposed into the subretinal space (82) of the eye and are used to stimulate those retinas where the photoreceptor layer has completely degenerated leaving the bipolar cell layer (58a) or the inner plexiform layer (56) as the layer adjacent to the subretinal space (82). Since the "light channel" inner plexiform layer known as sublamina "B" (56b) is further away from the subretinal space (82) compared to the "dark channel" inner plexiform layer known as sublamina "A" (56a), the HPE electrodes (202, 302) will selectively contact the "light channel" synapses in the sublamina "B" (56b) and the LPEs (204, 304) will selectively contact the "dark channel" synapses in sublamina "A" (56A). This arrangement will allow a visible light stimulus to selectively depolarize and activate the light channels in sublamina "B" by causing a negative electric current to be produced by the HPE (202), and an IR light stimulus to selectively hyperpolarize and inhibit the light channels in sublamina "B" by causing a positive electric current to be produced by the HPE (302). This arrangement will also allow an IR light stimulus to selectively depolarize and activate the dark channels in sublamina "A" by causing a negative electric current to be produced by the LPE (304), and a visible light stimulus to selectively hyperpolarize and inhibit the dark channels in sublamina "A" by causing a positive electric current to be produced by the LPE (204).

Figure 22:
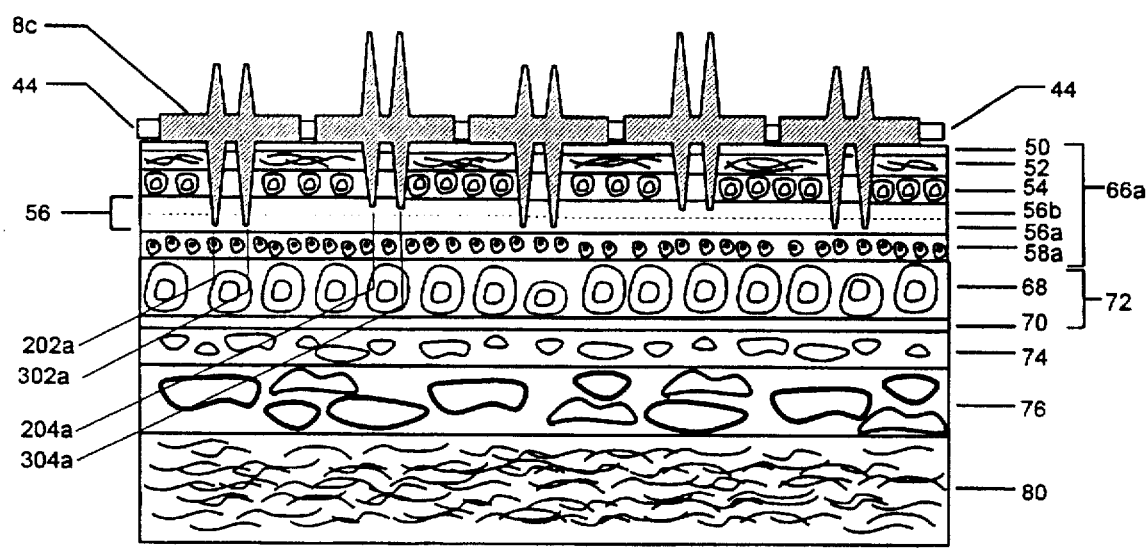
FIG. 22 is a cross-section of the retina showing the microphotodiode implants of FIG. 17 with reversed polarities (MMRI-IPVIR-AR), in a ninth embodiment of this invention, in their preferred location on the nerve fiber layer surface, with their electrodes penetrating into the sublamina B, and sublamina A location of the inner plexiform.

As illustrated in FIGS. 12 and 22, in another embodiment, MMRI-4 (8), and reversed polarity MMRI-IPVIR-A implants called for convenience, MMRI-IPVIR-ARs (8c), are embedded into a biologically compatible sheet (44) that allows the electrode surfaces of the devices to be exposed.

As shown in FIG. 12, the sheet (44), with the embedded MMRI-4 (8) is placed on the internal limiting membrane surface (50) of the retina from the vitreous body side. From this location, MMRI-4s (8) will stimulate the Nerve Fiber Layer (52) and/or Ganglion Cells (54) of the retina.

As shown in FIG. 22, in the case of the MMRI-IPVIR-ARs (8c), their electrodes will penetrate the nerve fiber (52) and ganglion cell layer (54) into the sublamina "B" light channel layer (56b), and sublamina "A" dark channel layer (56a) regions of the inner plexiform layer (56) to selectively stimulate those layers to induce visual sensations. The reverse polarity of the MMRI-IPVIR-ARs (8c) compared to the MMRI-IPVIR-As (400) of FIG. 21 is necessary to preserve the visible light stimulus's effect of depolarizing (activating) the light channels of sublamina "B" (56b) while hyperpolarizing (inhibiting) the dark channels of sublamina "A" (56a); and an IR light stimulus's effect of depolarizing (activating) the dark channels of sublamina "A" (56a) while hyperpolarizing (inhibiting) the light channels of sublamina "B" (56b). It should be noted that polarization changes, i.e. hyperpolarization and depolarization, do not have the same effect in the subretinal space on remanent photoreceptor cells as they do in the sublamina B and A regions of the IPL. In the subretinal space, a hyperpolarizing stimulus produces a sensation of light in the remanent photoreceptor cells while a depolarizing stimulus produces a sensation of darkness in remanent photoreceptor cells.

Figure 13:
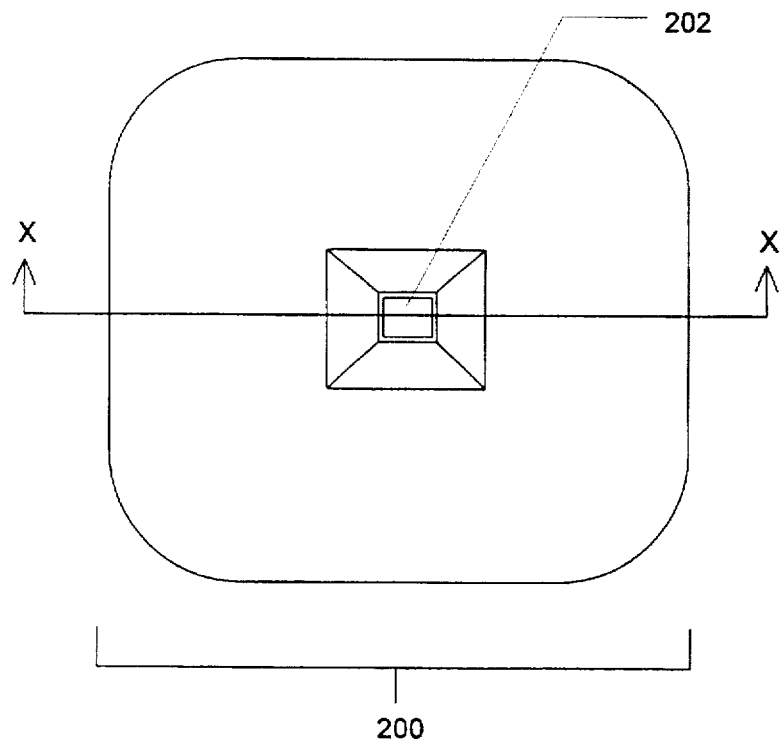
FIG. 13 shows a plan view of a fifth embodiment of the microphotodiode implant of this invention (MMRI-IPV)
Figure 14:
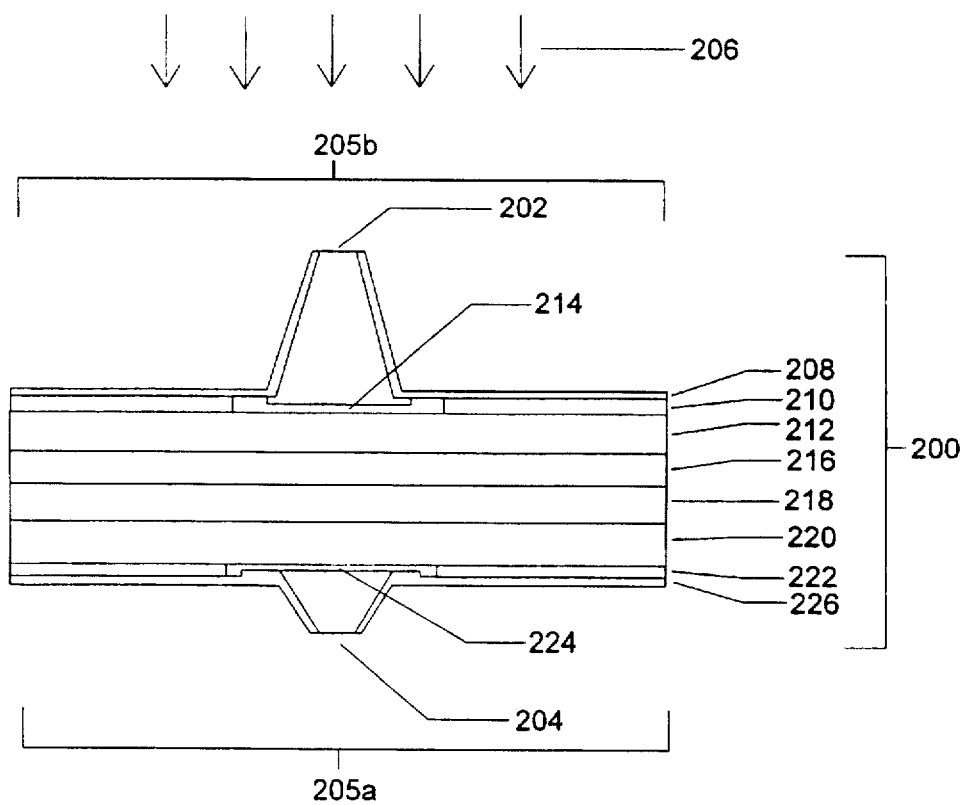
FIG. 14 is a cross-section take along the plane of line X—X of FIG. 13.

FIGS. 13–14 therefore illustrate a fifth embodiment of this invention referred to for convenience as a "MMRI-IPV", and is sized in microscopic dimensions, and is designated at (200). MMRI-IPV (200) is a physically independent unit with its layered microarchitecture shown in FIG. 14. In this embodiment, the MMRI-IPV (200) forms the shape of a flattened cube with rounded corners and edges, with an electrically negative high projecting electrode ("HPE") (202), and an electrically positive low projecting electrode ("LPE") (204). A MMRI-IPV (200) may function as a PiN or NiP device when stimulating the inner retina, depending upon which of its two photosensitive sides, the P side (205a) or the N side (205b) is stimulated by visible light (206). From top to bottom, the layers of the MMRI-IPV (200) are as follows: A negative HPE electrode (202) preferably made of gold, an insulating layer of SiO$_2$ (208) which covers the N side (205b) except for the tip of the HPE electrode (202), a multilayer dielectric filter (210) to allow passage of only visible light (400 nm to 740 nm), a N+ layer (212), a contact pad (214) fabricated from any of the following, and/or any compounds of the following: gold, aluminum, titanium, and chromium, to establish electrical contact between the negative HPE (202) and the N+ layer (212), a N-type silicon substrate layer (216), an intrinsic layer (218) which forms naturally between the N-type silicon substrate layer (216), and the next P+ layer (220), a multilayer dielectric filter (222) to allow passage of only visible light (400 nm to 740 nm), a contact pad (224) fabricated from any of the following, and/or any compounds of the following: gold, aluminum, titanium, and chromium to establish electrical contact between the P+ layer (220) and the electrically positive low projecting electrode (LPE) (204). An insulating layer of SiO$_2$ (226) covers the P side (205a) except for the tip of the LPE electrode (204).

Figure 15:
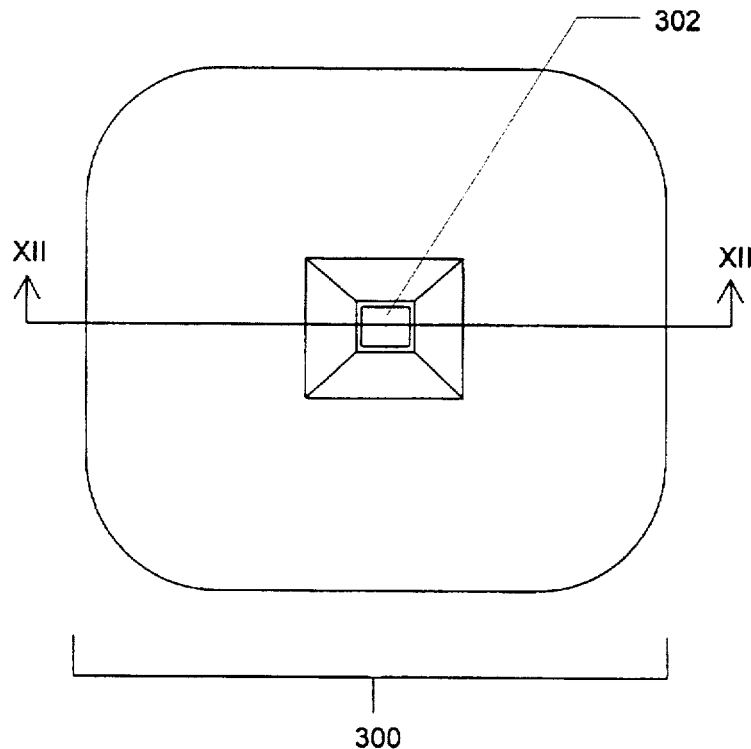
FIG. 15 shows a plan view of a sixth embodiment of the microphotodiode implant of this invention (MMRI-IPIR)
Figure 16:
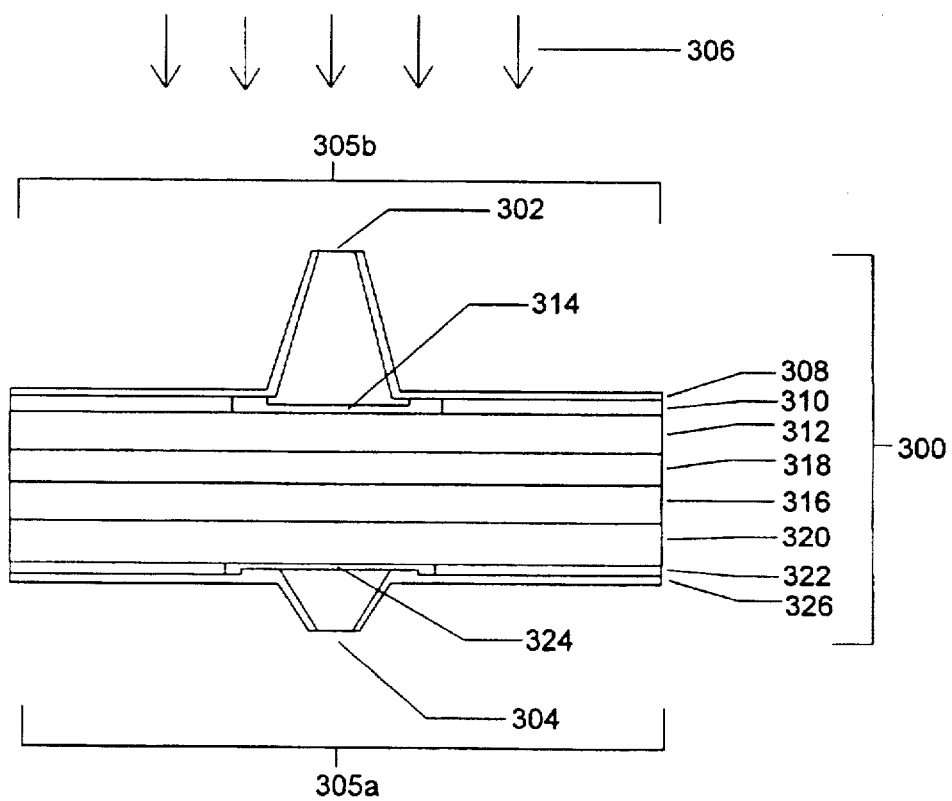
FIG. 16 is a cross-section taken along the plane of line XII—XII of FIG. 15.

FIGS. 15–16 illustrates a sixth embodiment of this invention referred to for convenience as a "MMRI-IPIR", and is sized in microscopic dimensions, and is designated at (300). As illustrated, a MMRI-IPIR (300) is a physically independent unit with its layered microarchitecture is shown in FIG. 16. In this embodiment, the MMRI-IPIR (300) forms the shape of a flattened cube with rounded corners and edges, with an electrically positive high projecting electrode (HPE) (302), and an electrically negative low projecting electrode (LPE) (304). The MMRI-IPIR (300) is sized in microscopic dimensions. A MMRI-IPIR (300) may function as a PiN or NiP device when stimulating the inner retina, depending upon which of its two photosensitive sides, the N-side (305a) or the P-side (305b) is stimulated by infrared light (306). From top to bottom, the layers of the MMRI-IPIR (300) are as follows: A positive HPE electrode (302) preferably made of gold, an insulating layer of SiO$_2$ (308) which covers the P side (305b) except for the tip of the positive HPE electrode (302), a multilayer dielectric filter (310) to allow passage of only IR light (740 nm to 900 nm), a P+ layer (312), a contact pad (314) fabricated from any of the following and/or any compounds of the following: gold, aluminum, titanium, and chromium, to establish electrical contact between the positive HPE (302) and the P+ layer (312), an intrinsic layer (318) which forms naturally between the P+ layer (312) and the next N-type silicon substrate layer (316), a N+ layer (320), a multilayer dielectric filter (322) to allow passage of only IR light (740 nm to 900 nm), a contact pad (324) fabricated from any of the following and/or any compounds of the following: gold, aluminum, titanium, and chromium to establish electrical contact between the N+ layer (320) and the electrically negative low projecting electrode (LPE) (304). An insulating layer of SiO$_2$ (326) covers the N side (305a) except for the tip of the LPE electrode (304).

FIGS. 17–18 illustrate a seventh embodiment of this invention referred to for convenience as a "MMRI-IPVIR- A", and is sized in microscopic dimensions, and is designated at 400. It is composed of one MMRI-IPV (200), and one MMRI-IPIR (300), separate by a layer of channel block (350). The layered microarchitecture of the MMRI-IPV component (200) is shown on the left side and is described first. The MMRI-IPV component (200) forms the shape of one-half of a flattened cube with rounded external corners and edges, with an electrically negative high projecting electrode (HPE) (202), and an electrically positive low projecting electrode (LPE) (204). From top to bottom, the layers of the MMRI-IPV (200) are as follows: A negative HPE electrode (202) preferably made of gold, an insulating layer of $SiO_2$ (208) which covers the N side (205b) except for the tip of the HPE electrode (202), a multilayer dielectric filter (210) to allow passage of only visible light (400 nm to 740 nm), a N+ layer (212), a contact pad (214) fabricated from any of the following and/or any compounds of the following: gold, aluminum, titanium, and chromium, to establish electrical contact between the negative HPE (202) and the N+ layer (212), a N-type silicon substrate layer (216), an intrinsic layer (218) which forms naturally between the N-type silicon substrate layer (216), and the next P+ layer (220), a multilayer dielectric filter (222) to allow passage of only visible light (400 nm to 740 nm), a contact pad (224) fabricated from any of the following and/or any compounds of the following: gold, aluminum, titanium, and chromium to establish electrical contact between the P+ layer (220) and the electrically positive low projecting electrode (LPE) (204). An insulating layer of $SiO_2$ (226) covers the P side (205a) except for the tip of the LPE electrode (204). The layered microarchitecture of the MMRI-IPIR component (300) of the MMRI-IPVIR-A (400) is shown on the right side and is now described. The MMRI-IPIR component (300) forms the shape of one-half of a flattened cube with rounded external corners and edges, with an electrically positive high projecting electrode (HPE) (302), and an electrically negative low projecting electrode (LPE) (304). From top to bottom, the layers of the MMRI-IPIR (300) are as follows: A positive HPE electrode (302) preferably made of gold, an insulating layer of $SiO_2$ (308) which covers the P side (305b) except for the tip of the positive HPE electrode (302), a multilayer dielectric filter (310) to allow passage of only IR light (740 nm to 900 nm), a P+ layer (312), a contact pad (314) fabricated from any of the following and/or any compounds of the following: gold, aluminum, titanium, and chromium, to establish electrical contact between the positive HPE (302) and the P+ layer (312), an intrinsic layer (318) which forms naturally between the P+ layer (312) and the next N-type silicon substrate layer (316), a N+ layer (320), a multilayer dielectric filter (322) to allow passage of only IR light (740 nm to 900 nm), a contact pad (324) fabricated from any of the following and/or any compounds of the following: gold, aluminum, titanium, and chromium to establish electrical contact between the N+ layer (320) and the electrically negative low projecting electrode (LPE) (304). An insulating layer of $SiO_2$ (326) covers the N side (305a) except for the tip of the LPE electrode (304).

Figure 19:
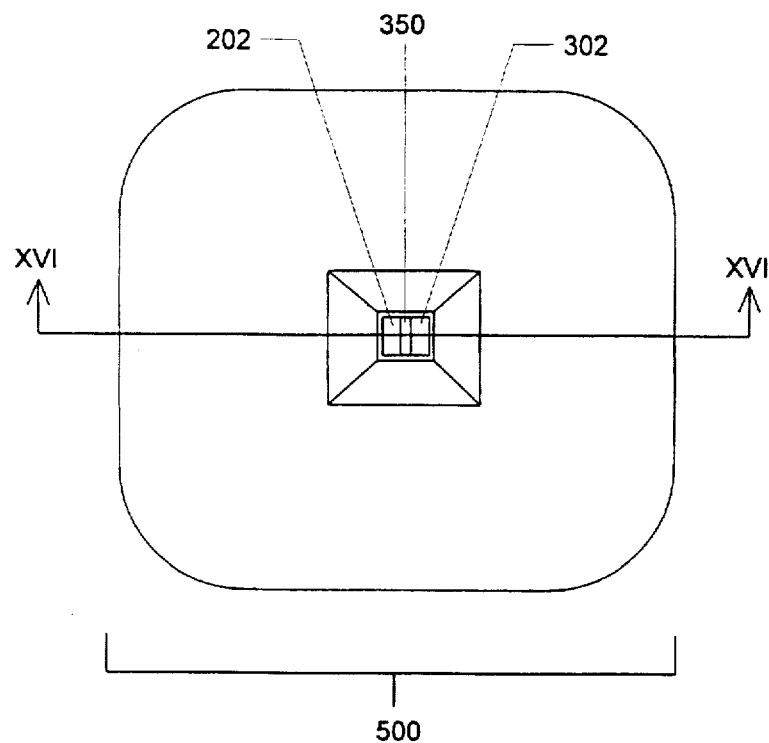
FIG. 19 shows a plan view of a eighth embodiment of the microphotodiode implant of this invention (MMRI-IPVIR-B)
Figure 20:
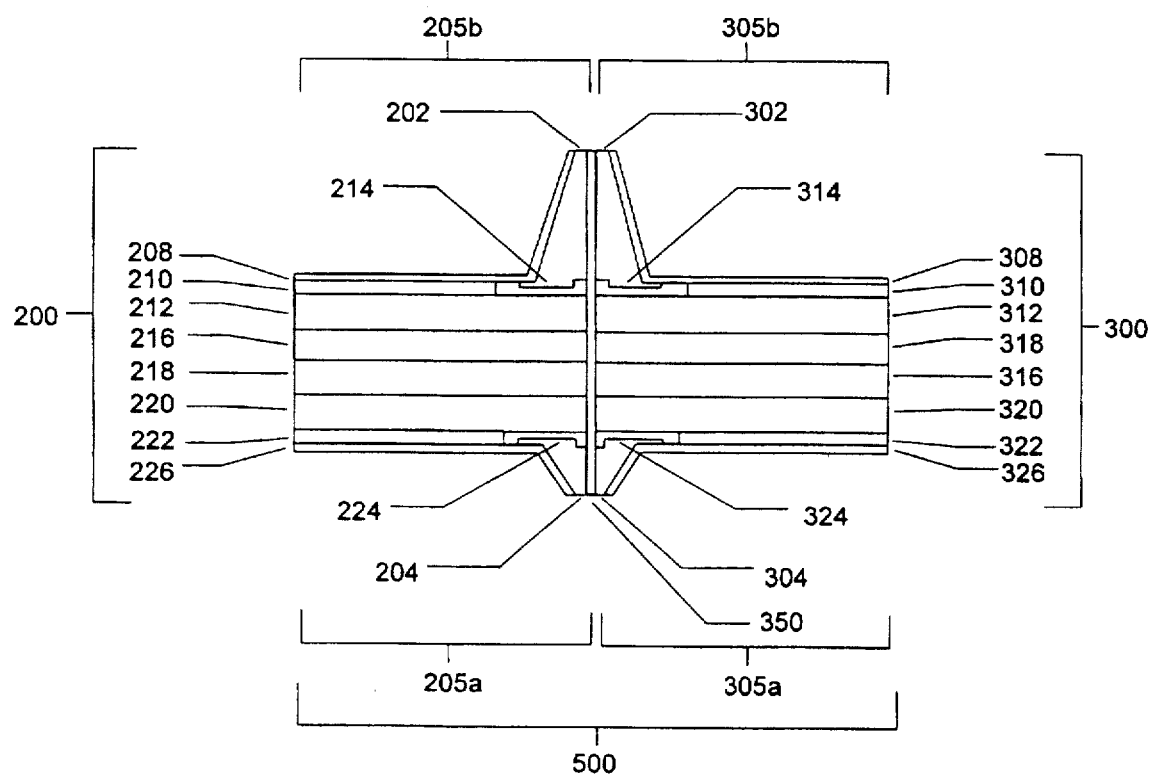
FIG. 20 is a cross-section taken along the plane of line XVI—XVI of FIG. 19.

FIGS. 19–20 illustrate an eighth embodiment of this invention referred to for convenience as a "MMRI-IPVIR-B", and is sized in microscopic dimensions, and is designated at 500. It is composed of one MMRI-IPV (200), and one MMRI-IPIR(300), separate by a layer of channel block (350). The layered microarchitecture of the MMRI-IPV component (200) is shown on the left side and is described first. The MMRI-IPV component (200) forms the shape of one-half of a flattened cube with rounded external corners and edges, with an electrically negative high projecting electrode (HPE) (202), and an electrically positive low projecting electrode (LPE) (204). From top to bottom, the layers of the MMRI-IPV (200) are as follows: A negative HPE electrode (202) preferably made of gold, an insulating layer of $SiO_2$ (208) which covers the N side (205b) except for the tip of the negative HPE electrode (202), a multilayer dielectric filter (210) to allow passage of only visible light (400 nm to 740 nm), a N+ layer (212), a contact pad (214) fabricated from any of the following and/or any compounds of the following: gold, aluminum, titanium, and chromium, to establish electrical contact between the negative HPE (202) and the N+ layer (212), a N-type silicon substrate layer (216), an intrinsic layer (218) which forms naturally between the N-type silicon substrate layer (216), and the next P+ layer (220), a multilayer dielectric filter (222) to allow passage of only visible light (400 nm to 740 nm), a contact pad (224) fabricated from any of the following and/or any compounds of the following: gold, aluminum, titanium, and chromium to establish electrical contact between the P+ layer (220) and the electrically positive low projecting electrode (LPE) (204). An insulating layer of $SiO_2$ (226) covers the P side (205a) except for the tip of the LPE electrode (204). The layered microarchitecture of the MMRI-IPIR component (300) of the MMRI-IPVIR-B (500) is shown on the right side and is now described. The MMRI-IPIR component (300) forms the shape of one-half of a flattened cube with rounded external corners and edges, with an electrically positive high projecting electrode (HPE) (302), and an electrically negative low projecting electrode (LPE) (304). From top to bottom, the layers of the MMRI-IPIR (300) are as follows: A positive HPE electrode (302) preferably made of gold, an insulating layer of $SiO_2$ (308) which covers the P side (305b) except for the tip of the positive HPE electrode (302), a multilayer dielectric filter (310) to allow passage of only IR light (740 nm to 900 nm), a P+ layer (312), a contact pad (314) fabricated from any of the following and/or any compounds of the following: gold, aluminum, titanium, and chromium, to establish electrical contact between the positive HPE (302) and the P+ layer (312), an intrinsic layer (318) which forms naturally between the P+ layer (312) and the next N-type silicon substrate layer (316), a N+ layer (320), a multilayer dielectric filter (322) to allow passage of only IR light (740 nm to 900 nm), a contact pad (324) fabricated from any of the following and/or any compounds of the following: gold, aluminum, titanium, and chromium to establish electrical contact between the N+ layer (320) and the electrically negative low projecting electrode (LPE) (304). An insulating layer of $SiO_2$ (326) covers the N side (305a) except for the tip of the LPE electrode (304).

FIG. 21 shows MMRI-IPVIR-As (400) implanted in their preferred monolayer position in the subretinal space (82). The depolarizing high projecting electrodes (HPEs) (202) from the visible light sensing portion of the microphotodiodes stimulate the light channels in sublamina B (56b) of the inner plexiform layer (IPL) (56). The hyperpolarizing HPEs (302) from the IR light sensing portion of the microphotodiodes (for darkness detection) inhibit the light channels in sublamina B (56b) of the IPL (56). The depolarizing low projecting electrodes (LPEs) (304) from the IR light sensing portion of the microphotodiodes (for darkness detection) stimulate the dark channels in sublamina A (56a) of the IPL (56). The hyperpolaring LPEs (204) from the visible light sensing portion of the microphotodiode inhibit the dark channels in sublamina A (56a) of the IPL (56). The layers of the eye, in this schematic of a partially degenerated retina, at the posterior pole from inside the eye to outside the eye are: internal limiting membrane (50); nerve fiber layer (52); ganglion cell layer (54); inner plexiform layer (56) consisting of sublamina b (56b) and sublamina a (56a); and the partially degenerated inner nuclear layer (58a). The MMRI-IPVIR-A (400) are disposed between the partially degenerated inner retinal layer (66a), and the retinal pigment epithelium (68) and Bruch's membrane (70), which together constitute the outer retinal layer (72). External to the outer retinal layer (72) are the choriocapillaris (74), choroid (76), and sclera (80). Alternatively, instead of MMRI-IPVIR-As (400), component MMRI-IPVs and MMRI-IPIRs of FIGS. 13–16, or MMRI-IPVIR-Bs of FIGS. 19–20 can be implanted into the subretinal space (82).

FIG. 22 shows MMRI-IPVIR-ARs (8c) in a ninth embodiment of this invention, positioned on the internal limiting membrane surface (50) of the retina. In this embodiment, MMRI-IPVIR-ARs (8c) are embedded into a flexible, biologically compatible sheet (44), which allows both of the photoactive surfaces and their projecting electrodes of each MMRI-IPVIR-ARs (8c) to be exposed. The depolarizing high projecting electrodes (HPEs) (302a) on the opposite side of the IR sensing microphotodiodes (for darkness detection) penetrate into the dark channels in sublamina A (56a) of the inner plexiform layer (IPL) (56) to stimulate the sensation of darkness. The hyperpolarizing HPEs (202a) on the opposite side of the visible light sensing portion of the microphotodiodes penetrate into the sublamina A (56a) of the IPL (56) to inhibit the dark channels. The depolarizing low projecting electrodes (LPEs) (204a) on the opposite side of the visible light sensing portion of the microphotodiodes penetrate into sublamina B (56b) of the IPL (56) to stimulate the light channels. The hyperpolaring LPEs (304a) on the opposite side of the IR light sensing portion of the microphotodiode (for sensing darkness) penetrate into sublamina B (56b) of the IPL (56) to inhibit the light channels. The layers of the eye at the posterior pole from inside the eye to outside the eye in this schematic of a partially degenerated retina are: internal limiting membrane (50); nerve fiber layer (52); ganglion cell layer (54); inner plexiform layer (56) consisting of sublamina b (56b) and sublamina a (56a); the partially degenerated inner nuclear layer (58a); all of which constitute the partially degenerated inner retinal layer (66a). The retinal pigment epithelium (68) and Bruch's membrane (70), together constitute the outer retinal layer (72). External to the outer retinal layer (72) are the choriocapillaris (74), choroid (76), and sclera (80). In a subset embodiment, MMRI-IPVIR-ARs (8c) may be fabricated as component opposite polarity MMRI-IPVs and component opposite polarity MMRI-IPIRs, embedded into a flexible, biologically compatible sheet (44), which allows both of the photoactive surfaces and their projecting electrodes of each opposite polarity MMRI-IPV and opposite polarity MMRI-IPIR to be exposed.

Figure 23:
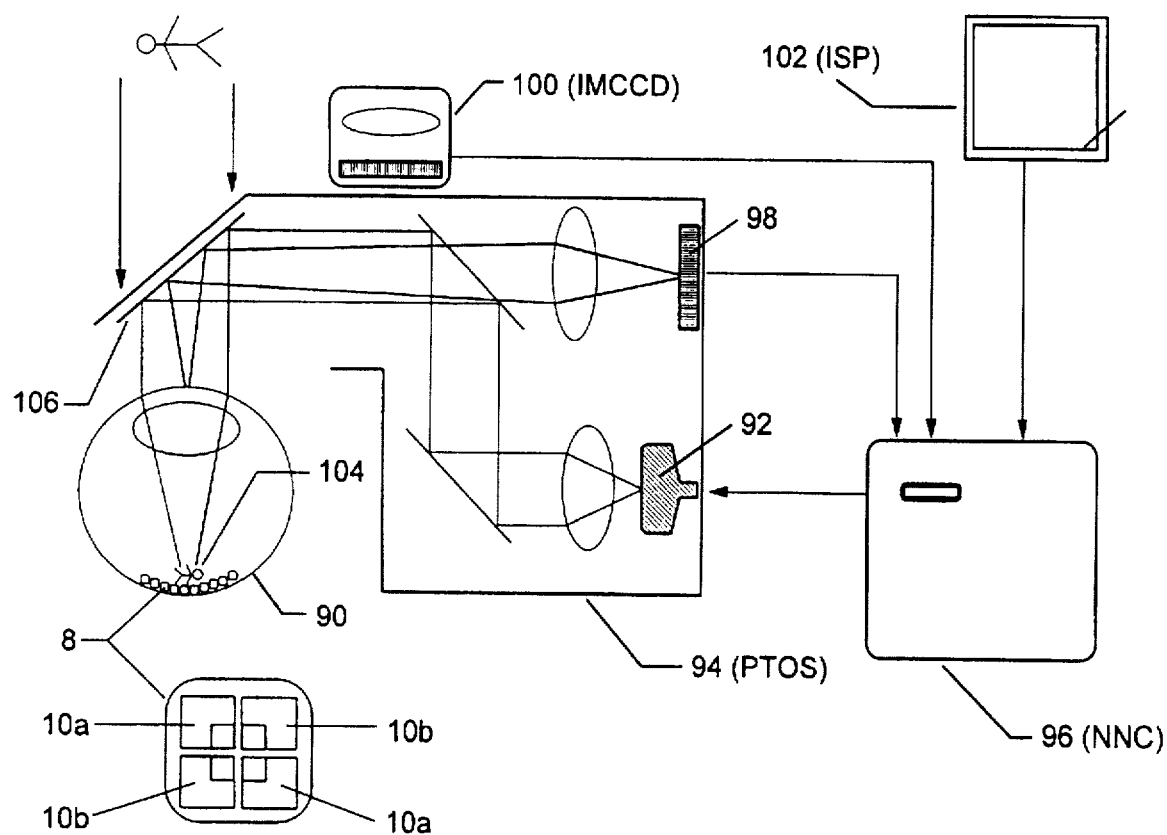
FIG. 23 is a generalized schematic diagram of the Adaptive Imaging Retinal Stimulation System (AIRES) showing its component sub-systems of: the Projection and Tracking Optical System (PTOS), the Neuro-Net Computer (NNC), and the Input Stylus Pad (ISP). Q-SEMCPs are shown implanted in the eye.

FIG. 23 is a schematic diagram of the Adaptive Imaging Retinal Stimulation System (AIRES) showing its component sub-systems of: the Projection and Tracking Optical System (PTOS) headset (94), the Neuro-Net Computer (NNC) (96), the Imaging CCD Camera (IMCCD) (100) and the Input Stylus Pad (ISP) (102). A Pupil Reflex Tracking CCD (PRTCCD) (98), and an IR/visible CRT display (IRVCRT) (92) is inside the PTOS (94). MMRI-4s (8) are shown in the subretinal space of the eye (90). During function, IR and visible light images from the IRVCRT (92) within the PTOS (94) are optically projected onto the eye (90). Intensity, wavelength duration, and pulsing of the images is controlled by the NNC (96) and modulated by patient inputs via the interfaced ISP (102). The IMCCD (100), which is mounted on or in the PTOS headset (94), provides the image inputs to the NNC (96) which in turn programs the visible and IR image outputs of the IRVCRT (92). A PRTCCD (98) is integrated into the PTOS headset (94) to track eye movements via changes in the position of the pupillary Purkinje reflexes. The PRTCCD (98) will output to the NNC (96) which in turn will direct the aim of the IMCCD (100) via servo motor control to follow the eye movements. The PTOS (94) also may be programmed to provide just a diffuse IR illumination to interact with ambient visible light images (104) on the MMRI-4s (8).

The detailed operation of the AIRES system is as follows. A patient with a large plurality of implanted MMRI-4s (8) will see pixelated images, cause by localized subretinal hyperpolarization, produced by the PiN configuration of the MMRI-4 subunits (10a). These electrically induced images are caused by the light from incoming ambient images (104) which pass through an external partially reflective and transmissive mirror (106) of the PTOS (94). Images of dark details are induced by depolarizing currents produced by the NiP configuration of MMRI-4 subunits (10b), which are stimulated by IR illumination and/or images provided by the IRVCRT (92). The IRVCRT (92) is programmed by the NNC (96) to provide diffuse IR illumination and/or IR images to superimpose upon the visible light images (104) from incoming light. Image information for the NNC (96) is obtained from the interfaced IMCCD (100). Diffuse IR illumination from the IRVCRT (92) will induce a constant depolarizing "bias current" from the MMRI-4 Nip subunits (10b). This "bias current" will produce the sensation of darkness in the absence of light stimulation to the PiN subunits (10a). However, when light is present to stimulate the PiN subunits (10a), the resultant hyperpolarizing current will offset the IR induced NiP depolarizing bias current. The result is the perception by the patient of a sensation of light. Because of the limited bandwidth sensitivity of the IR NiP configuration (10b) (740–900 nm), environmental IR "noise" is minimal. The amount of NiP depolarizing bias current will be initially adjusted by the patient via the ISP (102) and this information will be inputted into the NNC (96). It is then correlated with image processed information coming from the interfaced IMCCD (100). The appropriate amount of NiP "bias current", base upon environmental lighting conditions and images, will then be "learned" by the NNC (96). With additional learning, the NNC (96) will be able to anticipate the amount of NiP "bias current" needed to produce more accurate patient perceived images, without the need for patient input.

The entire visible light image may also be projected by the IRVCRT (92) simultaneously, or in rapid alternation with IR image pulses to entirely control MMRI-4(B) function. In this situation, the partially reflective/transmissive mirror (106) of the PTOS (94), is replaced with a completely reflective mirror, to prevent ambient light images (104) from stimulating the MMRI-4s (8). By programming the pulse duration and frequency of IR and visible-light images, color vision may possibly be induced, similar to the effect of the Benham top. This phenomenon has also been used in black and white television displays to create the perception of color images in normal sighted persons.

FIGS. 24. A through D shows a glasses-like configuration (94) of the PTOS component of the AIRES system. As seen in FIG. 24D, although the schematic of the optical system differs somewhat from the generalize schematic of the PTOS component (94) demonstrated in FIG. 23, the spirit and function of both versions of the devices are the same. FIG.

Figure 24D:
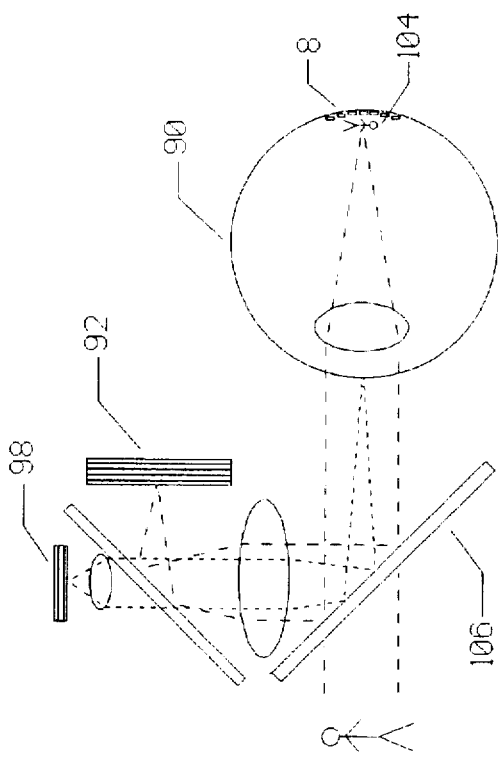
FIG. 24A–D shows a PTOS device configured as a glasses headset, and the schematic of its optics.
Figure 24C:
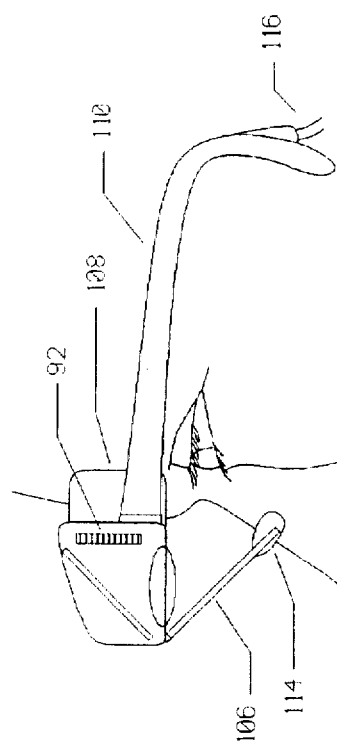
Figure 24A:
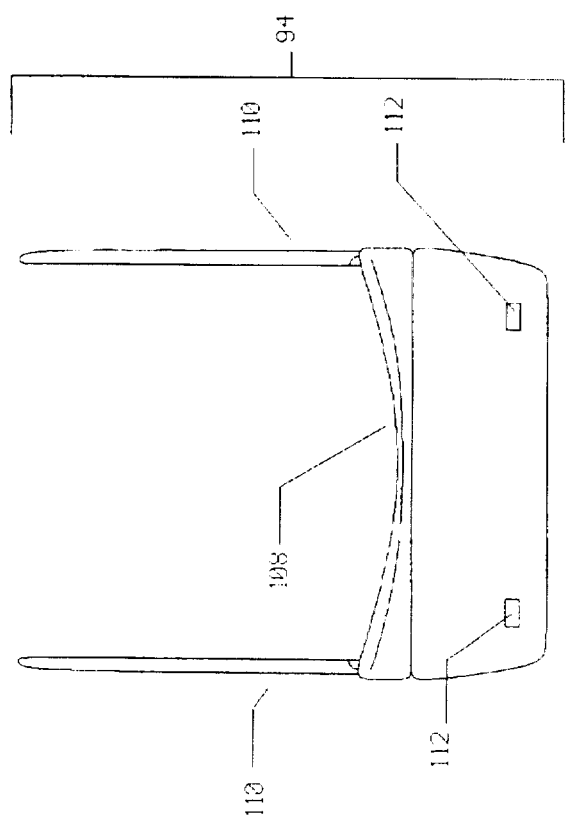
Figure 24B:
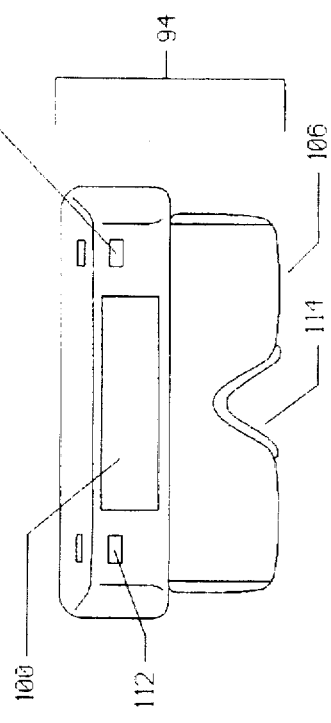

24A is a top view of the PTOS (94). It shows the headpad (108), the temple pieces (110), and the ambient light intensity sensors (112). FIG. 24B is a front view of the PTOS (94). It shows the external partially reflective/transmissive mirror (106), a supporting nose piece (114), ambient light intensity sensors (112), and the window for the IMCCD (100) shown in the FIG. 23 schematic. FIG. 24C is a phantom side view of the PTOS (94). It shows an internal infrared and visible light capable LED light source (92), which has been substituted for the IRVCRT (92) of FIG. 23. Also shown is the partially reflective/transmissive mirror (106), the supporting nose piece (114), the headpad (108), one of the temple pieces (110), and the power supply and signal wire cable (116) to the NNC (96) of FIG. 23. FIG. 24D is a schematic of the PTOS (94). It shows the MMRI-4s (8) disposed in the subretinal space of the eye (90) with an ambient focused image (104). It also shows the internal infrared and visible light capable LED light source (92), the PRTCCD (98), and the external partially reflective/transmissive mirror (106).

Figure 25:
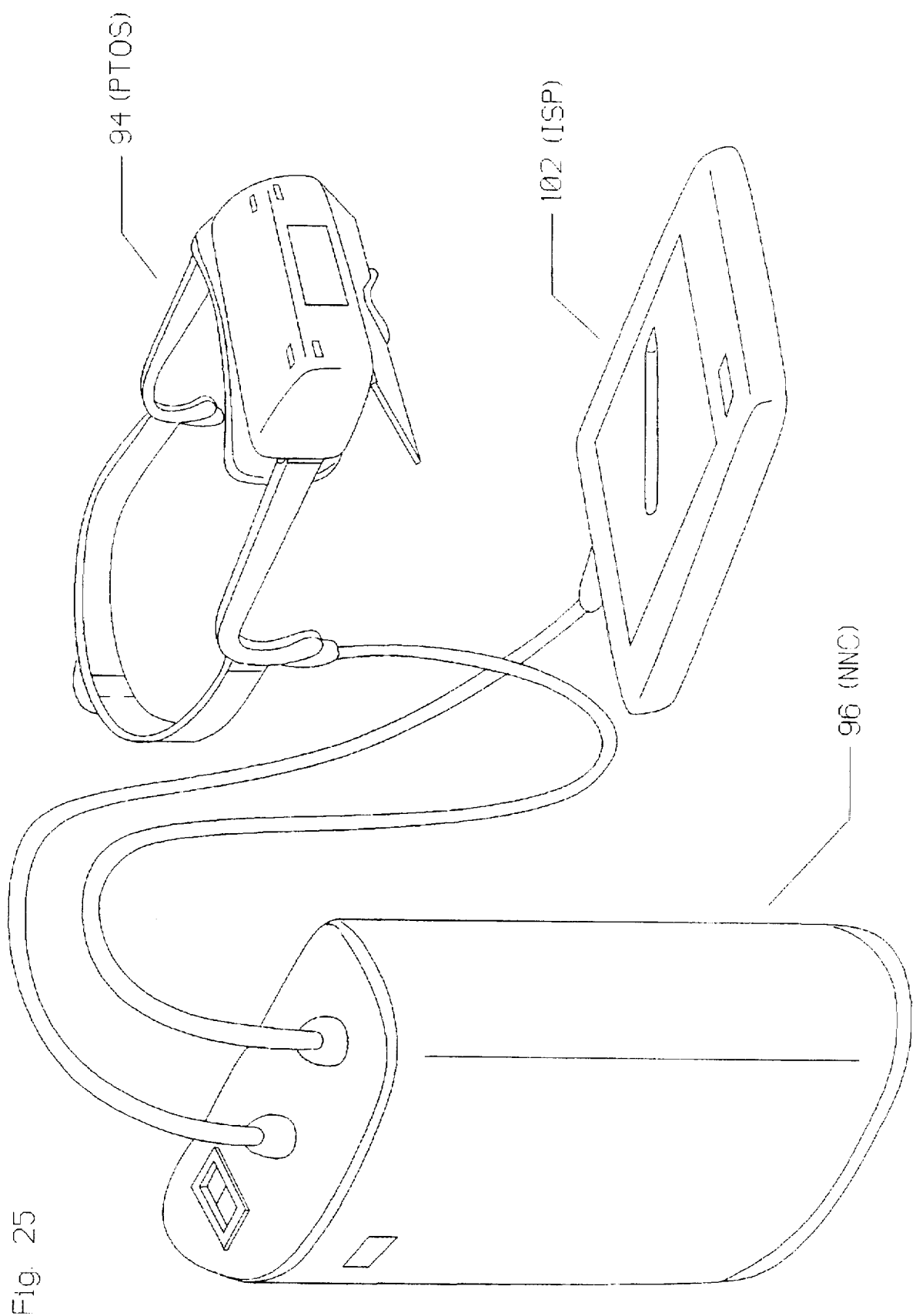
FIG. 25 shows the components of the AIRES system, consisting of the PTOS, the NNC, and ISP.

FIG. 25 is diagram showing the components of the AIRES system, consisting of the PTOS (94), the portable NNC (96) which may be secured to the patient's body, and the ISP (102) input device.

We claim:

1. A microscopic retinal implant for electrically inducing formed vision in the eye, comprising a PiN microphotodiode having a P-Side and an N-Side, where the P side of the implant has a light filter layer that selectively permits a selected bandwidth of the ultraviolet, visible, and infrared spectrum to pass, and where the N-side of the implant has a light filter layer that selectively permits a selected bandwidth of the ultraviolet, visible, and infrared spectrum to pass, whereby the retinal implant can stimulate the retina regardless of whether the P-side or the N-side is oriented toward light incident to the eye.

2. The microscopic retinal implant of claim 1 wherein the N-side and the P-side filter layers selectively permit substantially the same bandwidth to pass.

3. The microscopic implant of claim 2 wherein the N-side light filter layer is a dielectric filter that allows 740 nm to 900 nm to pass.

4. The microscopic implant of claim 3 wherein the P-side light filter layer is a dielectric filter that allows 740 nm to 900 nm to pass.

5. The microscopic implant of claim 2 wherein the N-side light filter layer is a dielectric filter that allows 400 nm to 740 nm to pass.

6. The microscopic implant of claim 5 wherein the P-side light filter layer is a dielectric filter that allows 400 nm to 740 nm to pass.

7. The microscopic retinal implant of claim 1 wherein the N-side and the P-side filter layers selectively permit substantially different bandwidth to pass.

8. The microscopic implant of claim 7 wherein the N-side light filter layer is a dielectric filter that allows 740 nm to 900 nm to pass.

9. The microscopic implant of claim 8 wherein the P-side light filter layer is a dielectric filter that allows 400 nm to 740 nm to pass.

10. The microscopic implant of claim 7 wherein the N-side light filter layer is a dielectric filter that allows 400 nm to 740 nm to pass.

11. The microscopic implant of claim 10 wherein the P-side light filter layer is a dielectric filter that allows 740 nm to 900 nm to pass.

12. The microscopic retinal implant of claim 1 wherein the PiN microphotodiode contains (1) a P-electrode made of P-doped polysilicon, (2) a P-side light filter dielectric layer, (3) a P+ layer, (4) an intrinsic layer, (5) a N-type silicon substrate, (6) a N+ layer, (7) a N-side light filter dielectric layer, and (8) a N-electrode made of a N-doped polysilicon.

13. The microscopic retina implant of claim 12 wherein the implant further includes a first electrical contact pad that establishes electrical contact between the P-electrode and the P+ layer, and a second electrical contact pad that establishes electrical contact between the N-electrode and the N+ layer.

14. The microscopic retinal implant of claim 12 wherein, the P-electrode projects outwardly from the surface of the implant.

15. The microscopic retinal implant of claim 14 wherein, the N-electrode projects outwardly from the surface of the implant.

16. The microscopic retinal implant of claim 15 wherein, each of the P-electrode and N-electrode projects from about 1 micron to about 200 microns.

17. The microscopic retinal implant of claim 16 wherein, each of the P-electrode and N-electrode projects from about 2 micron to about 100 microns.

18. The microscopic retinal implant of claim 12 wherein, the N-electrode projects outwardly from the surface of the implant.

19. The microscopic implant of claim 1 wherein the implant includes two of said PiN microphotodiodes, each of the microphotodiodes having an opposite orientation from the other such that when implanted in the eye, the P-side of one microphotodiode will face incident light, and the N-side of the other microphotodiode will face incident light.

20. A method of restoring formed vision to a patient having retinal damage, comprising implanting plural implants into the patient's eye adjacent the retina, each implant comprising a PiN microphotodiode having a P-side and an N-side, where the P side of the implant has a light filter layer that selectively permits a selected bandwidth of the ultraviolet, visible, and infrared spectrum to pass, and where the N-side of the implant has a light filter layer that selectively permits a selected bandwidth of the ultraviolet, visible, and infrared spectrum to pass, whereby the retinal implant can stimulate the retina regardless of whether the P-side or the N-side is oriented toward light incident to the eye so that the patient can perceive visual forms.

21. The method of claim 20 where the P side of each implant has a light filter layer that selectively permits only visible light to pass, and where the N-side of each implant has a light filter layer that selectively permits only infrared light to pass.

22. The method of claim 21 wherein a population of such implants are implanted in the "subretinal space" between the outer and inner retina in the eye such that, randomly, about half of them (i.e. the first subpopulation) will be oriented so that the P sides face light incident to the eye, and about half (i.e the second subpopulation) will be oriented so that their N sides face incident light to the eye.

23. The method of claim 22 wherein the first subpopulation of microscopic implants convert energy from incoming visible light into small electrical currents to stimulate the sensation of light detail in the eye to produce formed vision, and the second subpopulation converts infrared light-induced electrical current to stimulate the retina with dark current to produce dark details.

24. The method of claim 23 wherein infrared light is introduced into the eye by an externally-worn unit containing an IR-capable image-producing device, whereby in darkness IR illumination is the predominate power source and powers the second subpopulation, stimulating the visual sensation of dark details.

25. The method of claim 24 wherein said IR-capable image-producing device is also visible-light capable wherein under conditions displaying light and dark details, a current will be induced in the first subpopulation by ambient visible light, and a current is induced in the second subpopulation by IR light, producing a combined perception of light and dark details.

26. The method of claim 25 wherein said externally-worn unit further includes an imaging CCD camera to capture real-time images, and further includes computer means to digitize those images and transmit those images to said image-producing device.

27. The method of claim 26 wherein said real-time images produced by the IR-capable/visible light-capable image-producing device are presented to the retina superimposed on visible and infrared real, ambient images received directly by the implants from ambient incident light.

28. The method of claim 27 wherein the images produced by IR-capable/visible light-capable image-producing device are presented to the retina either simultaneously or in rapid succession with real, ambient images received directly by the implants from ambient incident light.

29. The method of claim 28 wherein the patient is provided with a patient input device interfaced with the computer means to allow the patient to modify the IR and visible-light images produced by said externally-worn unit.

30. The method of claim 20 comprising implanting a population of such implants in the subretinal space between the outer and inner retina in the eye such that, randomly, about half of them (i.e. the first subpopulation) will be oriented so that the P sides face light incident to the eye, and about half (i.e. the second subpopulation) will be oriented so that their N sides face incident light to the eye.

31. An implant for creating formed vision in the eye, comprising at least two microphotodiode subunits with one being PiN and the other being NiP, so that each of the two subunits has opposite PiN and NiP orientations whereby when the implant is placed in the eye so as to receive incident light, one of the subunits has a PiN configuration relative to incident light and the other subunit has a NiP configuration relative to incident light.

32. The implant as recited in claim 31 wherein the two subunits are symmetrical and have positive pole electrodes on opposite surfaces of the implant and negative pole electrodes on opposite surfaces of the implant, whereby the implant can function in the same manner regardless of which of the two surfaces faces light incident to the eye.

33. The implant as recited in claim 32 wherein the implant comprises two pairs of said two subunits.

34. The implant as recited in claim 31 wherein the implant is between 1 micron and 1000 microns wide and long, and wherein the thickness of the implant is between about 1 to 500 percent of its width.

35. The implant as recited in claim 31 wherein the implant is between about 10 microns and about 50 microns wide and long, and wherein the thickness of the implant is between about 25 to 50 percent of its width.

36. A method of restoring formed vision to a patient having retinal damage, comprising implanting plural implants into the patient's eye adjacent the retina, each implant comprising at least two microphotodiode subunits, each of the two subunits having opposite PiN and NiP orientations whereby when the implant is placed in the eye so as to receive incident light, one of the subunits has a PiN configuration relative to incident light and the other subunit has a NiP configuration relative to incident light.

37. The method of claim 36 wherein the two subunits of each implant are symmetrical and have positive pole electrodes on opposite surfaces of the implant and negative pole electrodes on opposite surfaces of the implant, whereby the implant can function in the same manner regardless of which of the two surfaces faces light incident to the eye.

38. The method of claim 37 wherein each implant comprises plural pairs of said two subunits.

39. The method of claim 38 wherein each implant comprises two pairs of said two subunits.

40. The method of claim 36 wherein each implant is between 1 micron and 1000 microns wide and long, and wherein the thickness of the implant is between about 1 to 500 percent of its width.

41. The method of claim 40 wherein the implant is between 10 and 50 microns wide and long, and wherein the thickness of the implant is between about 25 and 50 percent of its width.

42. The method of claim 40, comprising embedding a plurality of said implants into a biologically compatible sheet, and placing the sheet with the embedded implants in the subretinal space.

43. The method of claim 42 comprising placing the sheet with the embedded implants on the nerve fiber layer surface from the vitreous side.

44. The method of claim 43 wherein the sheet is fabricated from a biologically degradable material.

45. The method of claim 36 comprising implanting said implants on the nerve fiber layer surface.

46. A method of restoring formed vision to a patient having retinal damage, comprising implanting plural implants into the patient's eye on the nerve fiber layer, each implant comprising a PiN microphotodiode having a P-electrode and an N-electrode, where the P and the N electrodes each contain a projection such that the at least some of the P and the N electrodes of the plural implants penetrate into each of the sublamina A and B layers of the inner plexiform layer.

* * * * *